(12) United States Patent
Eaddy, III et al.

(10) Patent No.: US 7,442,833 B2
(45) Date of Patent: Oct. 28, 2008

(54) TRIPHENYLETHYLENE COMPOUNDS AS SELECTIVE ESTROGEN RECEPTOR MODULATORS

(75) Inventors: John Fred Eaddy, III, Durham, NC (US); Dennis Heyer, Durham, NC (US); Amarjit Sab Randhawa, Durham, NC (US); Vicente Samano, Durham, NC (US); John Albert Ray, Durham, NC (US); Subba Reddy Katamreddy, Durham, NC (US); Michael Tolar Martin, Durham, NC (US); Michael Scott McClure, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 56 days.

(21) Appl. No.: 10/575,038

(22) PCT Filed: Oct. 4, 2004

(86) PCT No.: PCT/US2004/032918

§ 371 (c)(1),
(2), (4) Date: Apr. 6, 2006

(87) PCT Pub. No.: WO2005/033056

PCT Pub. Date: Apr. 14, 2005

(65) Prior Publication Data

US 2007/0111971 A1    May 17, 2007

Related U.S. Application Data

(60) Provisional application No. 60/514,692, filed on Oct. 27, 2003, provisional application No. 60/509,678, filed on Oct. 8, 2003.

(51) Int. Cl.
*C07C 63/33* (2006.01)
*A61K 31/19* (2006.01)

(52) U.S. Cl. .................................... 562/491; 514/570
(58) Field of Classification Search ............ 560/1, 560/96, 899, 101; 562/468; 514/237.5
See application file for complete search history.

(56) References Cited

FOREIGN PATENT DOCUMENTS

| WO | WO-92/04310 A | 3/1992 |
|---|---|---|
| WO | WO-01/77055 A | 10/2001 |
| WO | WO-01/77057 A | 10/2001 |
| WO | WO-03/016270 A | 2/2003 |

OTHER PUBLICATIONS

Ross V. Weatherman, Nicola J. Clegg, Thomas S Scanlan Differential SERM activation of the estrogen receptors (ERalpha and ER beta) at AP-1 sites Chemistry and Biology 8 (2001) 427-436.*
Ross V. Weatherman, Nicola J. Clegg, Thomas S. Scanlan Differential SERM activation of the estrogen receptors (ERalpha and ERbeta) at AP-1 sites Ross V. Weatherman, Nicola J. Clegg, Thomas S. Scanlan Chemistry and Biology 8 (2001) 427-436.*
Scanlan T S et al.; Differential SERM Activation of the Estrogen Receptors (ERalpha and ERbeta) at AP-1 Sites; Chemistry and Biology, Current Biology; 2001; vol. 8, No. 5; 427-436; London, GB.
Willson T. M. et al.; 3-U4-(1,2-Diphenylbut-1-enyl)phenylacrylic Acid: A Non-Steroidal Estrogen with Functional Selectivity for Bone over Uterus in Rate; Journal of Medicinal Chemistry; May 25, 1994; vol. 37, No. 11; 1550-1552; American Chemical Society; Washington, US.
European Office Action for Application 04809876.8-2117 (Corresponding Application to U.S. Appl. No. 10/575,038).; Apr. 27, 2007.

* cited by examiner

*Primary Examiner*—Karl J Puttlitz
(74) *Attorney, Agent, or Firm*—J. Scott Young

(57) ABSTRACT

Compounds of formula (I):

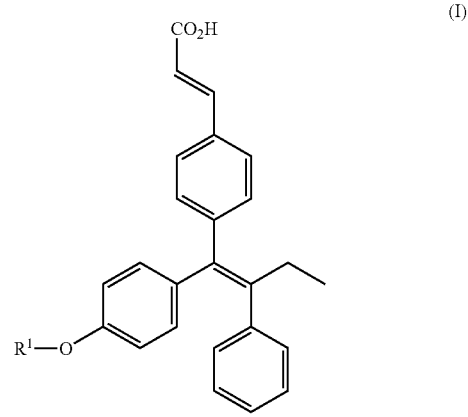

with a variety of therapeutic uses, more particularly novel prodrugs that are particularly useful for delivering a parent compound for selective estrogen receptor modulation.

21 Claims, No Drawings

TRIPHENYLETHYLENE COMPOUNDS AS SELECTIVE ESTROGEN RECEPTOR MODULATORS

CROSS-REFERENCE TO RELATED APPLICATIONS

This application is filed pursuant to 35 USC 371 as a United States National Phase Application of International Patent Application Serial No. PCT/US2004/032918 filed on Oct. 4, 2004, which claims priority from 60/509,678 filed on Oct. 8, 2003 and 60/514,692 filed on Oct. 27, 2003 in the United States.

FIELD OF THE INVENTION

The present invention relates to novel compounds with a variety of therapeutic uses, more particularly novel prodrugs represented by Formula I that deliver a parent compound (herein also referred to as compound 1), a compound that is particularly useful for selective estrogen receptor modulation. The present invention provides compounds that are characterized by unexpectedly oral bioavailability and unpredictably facile in vivo generation of the active (also referred to as "parent") compound. The present invention also relates to pharmaceutical compositions comprising these prodrugs.

BACKGROUND OF THE INVENTION

Estrogens are well-known endocrine regulators in the cellular processes involved in the development and maintenance of the reproductive system. Estrogens have also been shown to have important effects in many non-reproductive tissues such as bone, liver, the cardiovascular system, and the central nervous system. The most widely accepted hypothesis of how estrogens exert their effects is by binding to an intracellular steroid hormone receptor. After the receptor and bound ligand are transferred to the nucleus of the cell, the complex binds to recognition sites in DNA, which allows for the modulation of certain genes. Additionally, it is now becoming apparent that estrogens may mediate their effects via membrane-initiated signaling cascade, though much of this work is still experimental. Kousteni et al., *Journal of Clinical Investigation*, (2003), 111, 1651-1664, herein incorporated by reference with regard to such teaching.

Certain substances have demonstrated the ability to exhibit their biological activity in a "tissue-selective" manner. In other words, tissue selectivity allows functionality as estrogen agonists in certain tissues, while acting as estrogen antagonists in other tissues. The term "selective estrogen receptor modulators" (SERMs) has been given to these molecules. Examples of SERMs include tamoxifen, raloxifene, lasofoxifene, clomiphene, and nafoxidine. The molecular basis for this tissue-selective activity is not completely understood. Without being limited to any particular theory, the ability of the ligand to place the estrogen receptor into different conformational states and allowing for differential capabilities in recruiting coactivator and corepressor proteins, as well as other important proteins involved in transcriptional regulation, is believed to play a role. See, McDonnell, D. P., *The Molecular Pharmacology of SERMs*, Trends Endocrinol. Metab. 1999, 301-311, herein incorporated by reference with regard to such description.

Historically estrogens were believed to manifest their biological activity through a single estrogen receptor, now termed estrogen receptor alpha (ERα). More recently, however, there was the discovery of second subtype of estrogen receptor, termed estrogen receptor beta (ERβ). See, Kuiper et al., WO 97/09348 and Kuiper et al., *Cloning of a Novel Estrogen Receptor Expressed in Rat Prostate and Ovary*, Proc. Natl. Acad. Sci. U.S.A., 1996, pp. 5925-5930, each herein incorporated by reference with regard to such subtype. ERβ is expressed in humans. See, Mosselman et al., *ERβ: Identification and Characterization of a Novel Human Estrogen Receptor*, FEBS Lett., 1996, pp. 49-53, herein incorporated by reference with regard to such expression. The discovery of this second subtype of estrogen receptor significantly increased the biological complexity of estrogen signaling and may be responsible for some of the tissue-selective actions of the currently available SERMs.

As noted above, estrogens have important effects in many non-reproductive tissues. Thus, estrogen modulation is believed useful in the treatment or prophylaxis of diseases and conditions associated with such tissues, including bone, liver, and the central nervous system.

For example, osteoporosis is characterized by the net loss of bone mass per unit volume. Such bone loss results in a failure of the skeleton to provide adequate structural support for the body, thereby creating an increased risk of fracture. One of the most common types of osteoporosis is postmenopausal osteoporosis, which is associated with accelerated bone loss subsequent to cessation of menses and declining levels of endogenous estrogen in women. There is an inverse relationship between densitometric measures of bone mass and fracture risk, for peri- and postmenopausal women in the process of rapid bone loss due to declining levels of estrogen. See, Slemenda, et al., *Predictors of Bone Mass in Perimenopausal Women, A Prospective Study of Clinical Data Using Photon Absorptiometry*, Ann. Intern. Med., 1990, pp. 96-101 and Marshall, et al., *Meta-Analysis of How Well Measures of Bone Mineral Density Predict Occurrence of Osteoporotic Fractures*, Br. Med. J., 1996, pp. 1254-1259, each of which is herein incorporated by reference with regard to such relationship. Elderly women currently have a lifetime risk of fractures of about 75%. In addition there is an approximate 40% risk of hip fracture for Caucasian women over age 50 in the United States. The economic burden from osteoporotic fractures is considerable because of the necessity of hospitalization. In addition, although osteoporosis is generally not thought of as life-threatening, the mortality within 4 months of hip fracture is currently approximately 20 to 30%. Current therapies for postmenopausal osteoporosis include hormone replacement therapy or treatment with other antiresorptive agents such as bisphosphonates or calcitonin. Similarly, SERMS have been shown to be effective in the treatment of postmenopausal osteoporosis (see, Lindsay, R.: *Sex steroids in the pathogenesis and prevention of osteoporosis*. In: Osteoporosis 1988. Etiology, Diagnosis and Management. Riggs B L (ed)I, Raven Press, New York, USA (1988):333-358; Barzel US: *Estrogens in the prevention and treatment of postmenopausal osteoporosis: a review. Am J. Med* (1988) 85:847-850; and Ettinger, B., Black, D. M., et al., *Reduction of Vertebral Fracture Risk in Postmenopausal Women with Osteoporosis Treated with Raloxifene, JAMA,* 1999, 282, 637-645, each of which is incorporated by reference with regard to such teaching).

As another example, the effects of estrogens on breast tissue, particularly breast cancer, have been well documented. For example, a previously identified SERM, tamoxifen, decreases the risk of recurrent breast cancer, contralateral breast cancer, and mortality as well as increases the disease-free survival rate of patients with breast cancer at multiple stages of the disease. See, Cosman, F., Lindsay, R. *Selective Estrogen Receptor Modulators: Clinical Spectrum*, Endocrine Rev., 1999, pp. 418-434, herein incorporated by reference with regard to such teaching. The profile of tamoxifen, however, is not ideal due to potential interactive properties on reproductive tissues, such as uterine tissues. There is room for an improved therapy for the treatment of such cancers, namely a SERM with no agonist properties on any reproductive tissues.

Cardiovascular disease is the leading cause of death among postmenopausal women. Until recently, the preponderance of data suggested that estrogen replacement therapy in postmenopausal women reduced the risk of cardiovascular disease, although some studies reported no beneficial effect on overall mortality. See, Barrett-Connor, E. et al., *The Potential of SERMs for Reducing the Risk of Coronary Heart Disease*, Trends Endocrinol. Metab., 1999, pp. 320-325, herein incorporated by reference. The mechanism(s) by which estrogens were believed to exert their beneficial effects on the cardiovascular system are not entirely clear. Potentially estrogen's effects on serum cholesterol and lipoproteins, antioxidant properties, vascular smooth muscle proliferation, and inhibition of arterial cholesterol accumulation were believed to play a role. Id. See also, Cosman, F., Lindsay, R. *Selective Estrogen Receptor Modulators: Clinical Spectrum*, Endocrine Rev., 1999, pp. 418-434, herein incorporated by reference. In light of the recent reports of the HERS II and WHI studies, however, continuous combined Hormone Therapy, namely, CEE+MPA [Conjugated Equine Estrogen+Medroxy Progesterone Acetate], confers no cardiovascular benefit in menopausal women. See, Hulley S., Grady, D., Bush, T., et al., *Randomized trial of estrogen plus progestin for secondary prevention of coronary heart disease in postmenopausal women*. Heart and Estrogen/progestin Replacement Study (HERS) Research Group. *J. Am. Med. Assoc.* (1998) 280:605-613 and Wassertheil-Smoller S., Hendrix, S. L., Limacher, M., et al., for the WHI Investigators. *Effect of estrogen plus progestin on stroke in postmenopausal women: the Women's Health Initiative: a randomized trial. JAMA* (2003) 289, 2673-2684, each herein incorporated by reference with regard to such teaching. To what extent these findings may be extrapolated to SERMs is an issue that remains to be determined.

Other therapeutic alternatives include estrogen replacement therapy and/or hormone replacement therapy ("HRT"), which may be useful in the treatment of vasomotor symptoms, genitourinary atrophy, depression, and diabetes. Over 75% of women experience vasomotor symptoms during the climacteric years. Clinical signs, such as vasomotor symptoms and genitourinary atrophy, abate upon treatment with estrogen replacement therapy. Sagraves, R., *J. Clin. Pharmacol.* (1995), 35(9 Suppl):2S-10S, herein incorporated by reference with regard to such teaching. Preliminary data suggest that estradiol may alleviate depression during perimenopause and that the combination of estrogens and selective serotonin reuptake inhibitors may alleviate depression during the postmenopausal period. Soares, C. N., Poitras, J. R., and Prouty, J., *Drugs Aging*, (2003), 20(2), 85-100, herein incorporated by reference with regard to such teaching. Furthermore, hormone replacement therapy may improve glycemic control among women with diabetes. Palin, S. L. et al., *Diabetes Research and Clinical Practice*, (2001), 54, 67-77; Ferrara, A. et al., *Diabetes Care*, (2001), 24(7), 1144-1150, each incorporated herein by reference with regard to such teaching. There is a need, however, for improved therapies that present better side effect profiles as compared to HRT.

The present inventors discovered a novel group of prodrugs that deliver a parent compound, or compound 1. The parent compound binds to and modulates estrogen receptor alpha ("ER-α") and estrogen receptor beta ("ER-β"). Thus, as a SERM, this compound is believed to be useful for the treatment and/or prophylaxis of, without limitation, menopausal or postmenopausal disorders, vasomotor symptoms, urogenital or vulvar vaginal atrophy, atrophic vaginitis, female sexual dysfunction, breast cancer, depressive symptoms, diabetes, bone demineralization, and the treatment and/or prevention of osteoporosis.

This parent compound 1 has poor bioavailability and, as such, is not viable for use as a pharmaceutical agent. The parent compound cannot be administered effectively by an oral route of administration because of poor systemic absorption. There exists a need, therefore, for one or more prodrug forms of compound 1 that can provide an appropriate profile for a commercial pharmaceutical agent, including but not limited to bioavailability, metabolism, stability, synthesis, and large-scale manufacture.

SUMMARY OF THE INVENTION

The present invention includes compounds of formula (I):

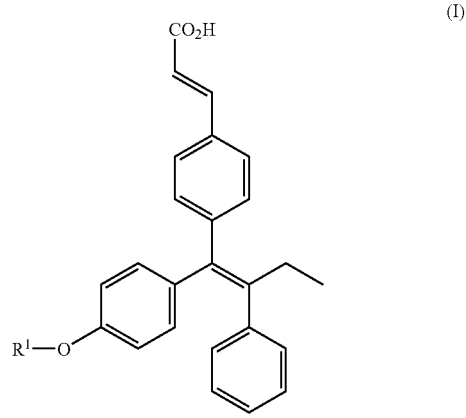

including salts, solvates, and pharmacologically functional derivatives thereof, wherein $R^1$ is —C(O)-alkyl, —C(O)-aryl, —C(O)-heteroaryl, —C(O)-cycloalkyl, —C(O)—$(CH_2)_n$—$NR^4R^5$, —C(O)—O-alkyl, —C(O)—$(CH_2)_n$—O-alkyl, —C(O)—$(CH_2)_n$-haloalkyl, —C(O)—$(CH_2)_n$-heterocylcyl, or —$PO_3H_2$;

$R^4$ and $R^5$ each independently are selected from H and alkyl; and n is 1 to 6.

Preferably alkyl is $C_1$-$C_6$ alkyl; aryl is phenyl; heteroaryl is thienyl, isoxazoyl, or furyl; cycloalkyl is $C_1$-$C_6$ cycloalkyl, haloalkyl is $C_1$-$C_6$ haloalkyl, and heterocyclyl is morpholinyl or optionally substituted piperizinyl.

More preferably $R^1$ is —C(O)—$C_{1-6}$alkyl. Still more preferably the compound of formula (I) is (2E)-3-(4-{(1Z)-2-phenyl-1-[4-(propionyloxy)phenyl]but-1-enyl}phenyl)prop-2-enoic acid.

Another aspect of the present invention includes compounds of formula (I)

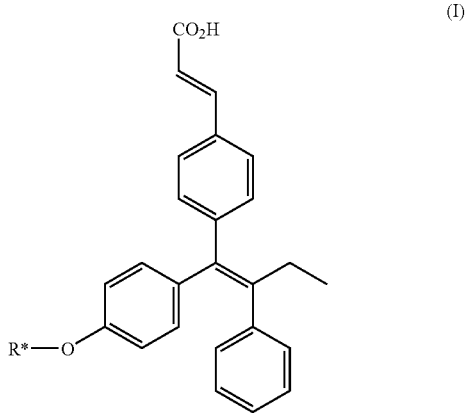

including salts, solvates, and pharmaceutically acceptable derivatives thereof, wherein R* is any prodrug moiety that provides an approximate 2.5 fold improvement in bioavailability in a rat over a parent compound 1:

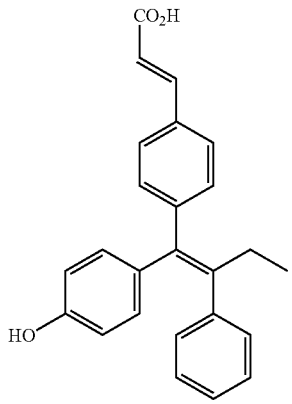

as measured in vivo when administered as a suspension in a pharmaceutically acceptable vehicle.

Preferably the bioavailability is provided through administration as a suspension in a vehicle composed of an aqueous solution containing 0.5% HPMC and 0.1% polysorbate 80.

Preferably R is —C(O)-alkyl, —C(O)-aryl, —C(O)-heteroaryl, —C(O)-cycloalkyl, —C(O)—$(CH_2)_n$—$NR^4R^5$—C(O)—O-alkyl, —C(O)—$(CH_2)_n$—O-alkyl, —C(O)—$(CH_2)_n$-haloalkyl, —C(O)—$(CH_2)_n$-heterocylcyl, or —$PO_3H_2$; $R^4$ and $R^5$ each independently are selected from H and alkyl; and n is 1 to 6.

Preferably the improvement is at least 10 fold. More preferably the improvement is about 15 fold.

Preferably R* is —C(O)—$CH_2$—$CH_3$.

Preferred compounds of the present invention include:
(2E)-3-(4-{(1Z)-2-phenyl-1-[4-(propionyloxy)phenyl]but-1-enyl}phenyl)prop-2-enoic acid;
(2E)-3-(4-{(1Z)-1-[4-(benzoyloxy)phenyl]-2-phenylbut-1-enyl}phenyl)prop-2-enoic acid;
(2E)-3-(4-{(1Z)-1-[4-(acetyloxy)phenyl]-2-phenylbut-1-enyl}phenyl)prop-2-enoic acid;
(2E)-3-(4-{(1Z)-1-[4-(butyryloxy)phenyl]-2-phenylbut-1-enyl}phenyl)prop-2-enoic acid;
(2E)-3-(4-{(1Z)-1-[4-(2-Furoyloxy)phenyl]-2-phenyl-1-butenyl}phenyl)-2-propenoic acid;
(2E)-3-[4-((1Z)-1-{4-[(N,N-dimethylglycyl)oxy]phenyl}-2-phenylbut-1-enyl)phenyl]prop-2-enoic acid;
(2E)-3-[4-((1Z)-1-{4-[(5-Isoxazolylcarbonyl)oxy]phenyl}-2-phenyl-1-butenyl)phenyl]-2-propenoic acid;
(2E)-3-[4-((1Z)-2-phenyl-1-{4-[(thien-2-ylcarbonyl)oxy]phenyl}but-1-enyl)phenyl]prop-2-enoic acid;
(2E)-3-[4-((1Z)-1-{4-[(methoxyacetyl)oxy]phenyl}-2-phenylbut-1-enyl)phenyl]prop-2-enoic acid;
(2E)-3-[4-((1Z)-2-phenyl-1-{4-[(4,4,4-trifluorobutanoyl)oxy]phenyl}but-1-enyl)phenyl]prop-2-enoic acid;
(2E)-3-[4-((1Z)-1-{4-[(2,2-dimethylpropanoyl)oxy]phenyl}-2-phenylbut-1-enyl)phenyl]prop-2-enoic acid;
(2E)-3-[4-((1Z)-1-{4-[(cyclohexylcarbonyl)oxy]phenyl}-2-phenyl but-1-enyl)phenyl]prop-2-enoic acid;
(2E)-3-[4-((1Z)-1-{4-[(morpholin-4-ylacetyl)oxy]phenyl}-2-phenylbut-1-enyl)phenyl]prop-2-enoic acid;
(2E)-3-[4-((1Z)-2-phenyl-1-{4-[(piperidin-1-ylacetyl)oxy]phenyl}but-1-enyl)phenyl]prop-2-enoic acid;
(2E)-3-{4-[(1Z)-1-(4-{[(4-methylpiperazin-1-yl)acetyl]oxy}phenyl)-2-phenylbut-1-enyl]phenyl}prop-2-enoic acid;
(2E)-3-(4-{(1Z)-2-Phenyl-1-[4-(phosphonooxy)phenyl]-1-butenyl}phenyl)-2-propenoic acid;
(2E)-3-[4-((1Z)-1-{4-[(Ethoxycarbonyl)oxy]phenyl}-2-phenyl-1-butenyl)phenyl]-2-propenoic acid; and
(2E)-3-[4-((1Z)-1-{4-[(Methoxycarbonyl)oxy]phenyl}-2-phenyl-1-butenyl)phenyl]-2-propenoic acid.

Another aspect of the present invention includes compounds of the present invention substantially as hereinbefore defined with reference to any one of the Examples.

Another aspect of the present invention includes pharmaceutical compositions comprising one or more compound according to the present invention, and one or more pharmaceutically acceptable carrier.

Another aspect of the present invention includes compounds according to the present invention for use as an active therapeutic substance.

Another aspect of the present invention includes compounds according to the present invention for use in the treatment or prophylaxis of conditions or disorders affected by selective estrogen receptor modulation.

Preferably the treatment or prophylaxis relates to osteoporosis, bone demineralization, reduced bone mass, density, or growth, osteoarthritis, acceleration of bone fracture repair and healing, acceleration of healing in joint replacement, periodontal disease, acceleration of tooth repair or growth, Paget's disease, osteochondrodysplasias, muscle wasting, the maintenance and enhancement of muscle strength and function, frailty or age-related functional decline ("ARFD"), sarcopenia, chronic fatigue syndrome, chronic myalgia, acute fatigue syndrome, acceleration of wound healing, maintenance of sensory function, chronic liver disease, AIDS, weightlessness, burn and trauma recovery, thrombocytopenia, short bowel syndrome, irritable bowel syndrome, inflammatory bowel disease, Crohn's disease and ulcerative colitis, obesity, eating disorders including anorexia associated with cachexia or aging, hypercortisolism and Cushing's syndrome, cardiovascular disease or cardiac dysfunction, congestive heart failure, high blood pressure, breast cancer, malignant tumor cells including breast, brain, skin, ovary, bladder, lymphatic, liver, kidney, uterine, pancreas, endometrium, lung, colon, and prostate, prostatic hyperplasia, hirsutism, acne, seborrhea, androgenic alopecia, anemia, hyperpilosity, adenomas and neoplasis of the prostate, hyperinsulinemia, insulin resistance, diabetes, syndrome X, dyslipidemia, urinary incontinence, artherosclerosis, libido enhancement, sexual dysfunction, depression, depressive symptoms, nervousness, irritability, stress, reduced mental energy and low self-esteem, improvement of cognitive function, endometriosis, polycystic ovary syndrome, counteracting preeclampsia, premenstral syndrome, contraception, uterine fibroid disease, and/or aortic smooth muscle cell proliferation, vaginal dryness, pruritis, dyspareunia, dysuria, frequent urination, urinary tract infections, hypercholesterolemia, hyperlipidemia, peripheral vascular disease, restenosis, vasospasm, vascular wall damage due to immune responses, Alzheimer's disease, bone disease, aging, inflammation, rheumatoid arthritis, respiratory disease, emphysema, reperfusion injury, viral hepatitis, tuberculosis, psoriasis, amyotrophic lateral sclerosis, stroke, CNS trauma, dementia, neurodegeneration, breast pain and dysmenorrhea, menopausal or postmenopausal disorders, vasomotor symptoms, urogenital or vulvar vaginal atrophy, atrophic vaginitis, female sexual dysfunction, for enhancing libido, for the treatment of hypoactive sexual disorder, sexual arousal disorder, for increasing the frequency and intensity of orgasms, vaginismus, osteopenia, endometriosis, BPH (benign prostatic hypertrophy), autoimmune diseases, Hashimoto's thyroiditis, SLE (systemic lupus erythematosus), myasthenia gravis, or reperfusion damage of ischemic myocardium.

Preferably the treatment or prophylaxis relates to menopausal or postmenopausal disorders, vasomotor symptoms, urogenital or vulvar vaginal atrophy, atrophic vaginitis, female sexual dysfunction, breast cancer, depressive symptoms, diabetes, bone demineralization, and/or osteoporosis.

Another aspect of the present invention includes the use of a compound according to the present invention in the manufacture of a medicament for use in the treatment or prophylaxis of conditions or disorders associated with selective estrogen receptor modulation.

Preferably, the use relates to the treatment or prophylaxis of osteoporosis, bone demineralization, reduced bone mass, density, or growth, osteoarthritis, acceleration of bone fracture repair and healing, acceleration of healing in joint replacement, periodontal disease, acceleration of tooth repair or growth, Paget's disease, osteochondrodysplasias, muscle wasting, the maintenance and enhancement of muscle strength and function, frailty or age-related functional decline ("ARFD"), sarcopenia, chronic fatigue syndrome, chronic myalgia, acute fatigue syndrome, acceleration of wound healing, maintenance of sensory function, chronic liver disease, AIDS, weightlessness, burn and trauma recovery, thrombocytopenia, short bowel syndrome, irritable bowel syndrome, inflammatory bowel disease, Crohn's disease and ulcerative colitis, obesity, eating disorders including anorexia associated with cachexia or aging, hypercortisolism and Cushing's syndrome, cardiovascular disease or cardiac dysfunction, congestive heart failure, high blood pressure, breast cancer, malignant tumor cells including breast, brain, skin, ovary, bladder, lymphatic, liver, kidney, uterine, pancreas, endometrium, lung, colon, and prostate, prostatic hyperplasia, hirsutism, acne, seborrhea, androgenic alopecia, anemia, hyperpilosity, adenomas and neoplasis of the prostate, hyperinsulinemia, insulin resistance, diabetes, syndrome X, dyslipidemia, urinary incontinence, artherosclerosis, libido enhancement, sexual dysfunction, depression, depressive symptoms, nervousness, irritability, stress, reduced mental energy and low self-esteem, improvement of cognitive function, endometriosis, polycystic ovary syndrome, counteracting preeclampsia, premenstral syndrome, contraception, uterine fibroid disease, and/or aortic smooth muscle cell proliferation, vaginal dryness, pruritus, dyspareunia, dysuria, frequent urination, urinary tract infections, hypercholesterolemia, hyperlipidemia, peripheral vascular disease, restenosis, vasospasm, vascular wall damage due to immune responses, Alzheimer's disease, bone disease, aging, inflammation, rheumatoid arthritis, respiratory disease, emphysema, reperfusion injury, viral hepatitis, tuberculosis, psoriasis, amyotrophic lateral sclerosis, stroke, CNS trauma, dementia, neurodegeneration, breast pain and dysmenorrhea, menopausal or postmenopausal disorders, vasomotor symptoms, urogenital or vulvar vaginal atrophy, atrophic vaginitis, female sexual dysfunction, for enhancing libido, for the treatment of hypoactive sexual disorder, sexual arousal disorder, for increasing the frequency and intensity of orgasms, vaginismus, osteopenia, endometriosis, BPH (benign prostatic hypertrophy), autoimmune diseases, Hashimoto's thyroiditis, SLE (systemic lupus erythematosus), myasthenia gravis, or reperfusion damage of ischemic myocardium.

Preferably the condition or disorder is menopausal or postmenopausal disorders, vasomotor symptoms, urogenital or vulvar vaginal atrophy, atrophic vaginitis, female sexual dysfunction, breast cancer, depressive symptoms, diabetes, bone demineralization, or osteoporosis.

Another aspect of the present invention includes methods for the treatment or prophylaxis of conditions or disorders associated with selective estrogen receptor modulation comprising the administration of a compound of the present invention.

Preferably the treatment or prophylaxis relates to osteoporosis, bone demineralization, reduced bone mass, density, or growth, osteoarthritis, acceleration of bone fracture repair and healing, acceleration of healing in joint replacement, periodontal disease, acceleration of tooth repair or growth, Paget's disease, osteochondrodysplasias, muscle wasting, the maintenance and enhancement of muscle strength and function, frailty or age-related functional decline ("ARFD"), sarcopenia, chronic fatigue syndrome, chronic myalgia, acute fatigue syndrome, acceleration of wound healing, maintenance of sensory function, chronic liver disease, AIDS, weightlessness, burn and trauma recovery, thrombocytopenia, short bowel syndrome, irritable bowel syndrome, inflammatory bowel disease, Crohn's disease and ulcerative colitis, obesity, eating disorders including anorexia associated with cachexia or aging, hypercortisolism and Cushing's syndrome, cardiovascular disease or cardiac dysfunction, congestive heart failure, high blood pressure, breast cancer, malignant tumor cells including breast, brain, skin, ovary, bladder, lymphatic, liver, kidney, uterine, pancreas, endometrium, lung, colon, and prostate, prostatic hyperplasia, hirsutism, acne, seborrhea, androgenic alopecia, anemia, hyperpilosity, adenomas and neoplasis of the prostate, hyperinsulinemia, insulin resistance, diabetes, syndrome X, dyslipidemia, urinary incontinence, artherosclerosis, libido enhancement, sexual dysfunction, depression, depressive symptoms, nervousness, irritability, stress, reduced mental energy and low self-esteem, improvement of cognitive function, endometriosis, polycystic ovary syndrome, counteracting preeclampsia, premenstral syndrome, contraception, uterine fibroid disease, and/or aortic smooth muscle cell proliferation, vaginal dryness, pruritus, dyspareunia, dysuria, frequent urination, urinary tract infections, hypercholesterolemia, hyperlipidemia, peripheral vascular disease, restenosis, vasospasm, vascular wall damage due to immune responses, Alzheimer's disease, bone disease, aging, inflammation, rheumatoid arthritis, respiratory disease, emphysema, reperfusion injury, viral hepatitis, tuberculosis, psoriasis, amyotrophic lateral sclerosis, stroke, CNS trauma, dementia, neurodegeneration, breast pain and dysmenorrhea, menopausal or postmenopausal disorders, vasomotor symptoms, urogenital or vulvar vaginal atrophy, atrophic vaginitis, female sexual dysfunction, for enhancing libido, for the treatment of hypoactive sexual disorder, sexual arousal disorder, for increasing the frequency and intensity of orgasms, vaginismus, osteopenia, endometriosis, BPH (benign prostatic hypertrophy), autoimmune diseases, Hashimoto's thyroiditis, SLE (systemic lupus erythematosus), myasthenia gravis, or reperfusion damage of ischemic myocardium comprising the administration of a compound of the present invention.

Preferably the condition or disorder is menopausal or postmenopausal disorders, vasomotor symptoms, urogenital or vulvar vaginal atrophy, atrophic vaginitis, female sexual dysfunction, breast cancer, depressive symptoms, diabetes, bone demineralization, or osteoporosis.

Another aspect of the present invention includes a process for making ester prodrugs of compound 1:

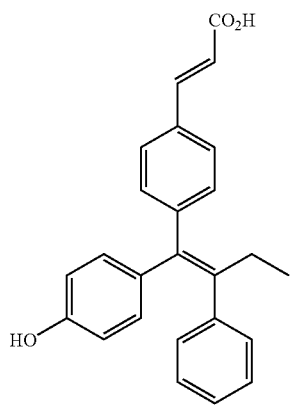

compound 1 that includes acylating anisole with 2-phenylbutanoic acid followed by demethylation to yield phenol 8:

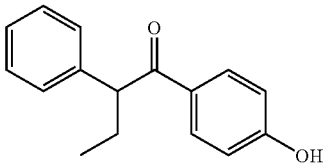

phenol 8 protecting the phenol group; treating the protected compound with an organometallic reagent, such as an organomagnesium or a lithium reagent, followed by dehydration to yield phenol aldehyde 10:

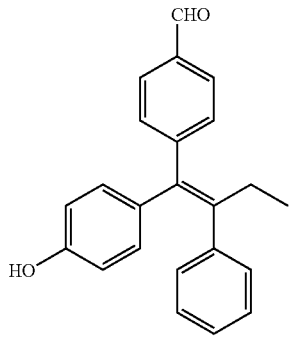

phenol aldehyde 10 acylating phenol aldehyde 10 with an anhydride or an acid chloride in the presence of a base to yield ester intermediate IV:

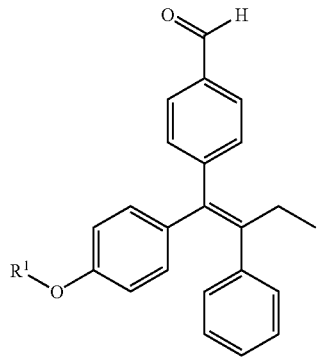

ester intermediate IV wherein $R^1$ is —C(O)-alkyl, —C(O)-aryl, —C(O)-heteroaryl, or —C(O)-cycloalkyl; and treating the ester intermediate IV with malonic acid to yield ester prodrug V:

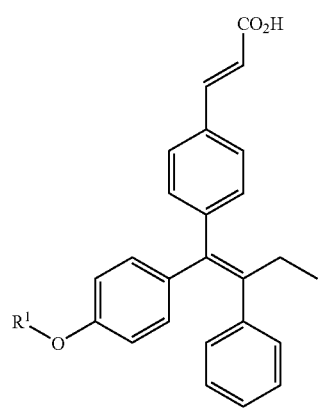

ester prodrug V wherein $R^1$ is as above-described. Preferably $R^1$ is —C(O)-alkyl. More preferably $R^1$ is —C(O)—$C_{1-6}$alkyl. More preferably $R^1$ is —C(O)—$CH_2CH_3$.

Preferably the step of acylating anisole with 2-phenylbutanoic acid further includes acid catalyzed acylation of anisole with the mixed anhydride of trifluoroacetic acid and 2-phenylbutanoic acid, followed by treatment with aluminum chloride in an appropriate solvent.

Preferably the step of protecting the phenol group of phenol 8 further includes protecting phenol 8 as a THP ether 9:

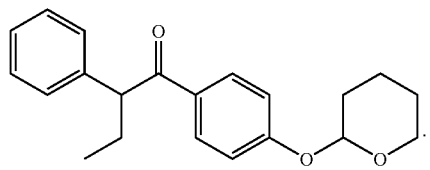

ether 9

More preferably the step of treating the protected compound with a lithium reagent further comprises treating ether 9 with [4-(dimethoxymethyl)phenyl] lithium or [4-(diethoxymethyl)phenyl] lithium followed by acid catalyzed dehydration.

Alternatively, as described in more detail hereinbelow, the step of acylating phenol aldehyde 10 with an anhydride or an acid chloride in the presence of a base to yield ester intermediate IV may instead be performed by treating the phenol aldehyde 10 with malonic acid to yield ester intermediate IV.

Another aspect of the present invention includes intermediates of formula IV:

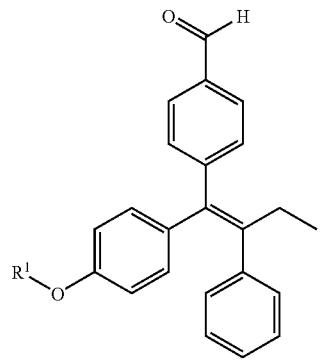

IV wherein R¹ is —C(O)-alkyl, —C(O)-aryl, —C(O)-heteroaryl, or —C(O)-cycloalkyl. Preferably R¹ is —C(O)-alkyl. Preferably R¹ is —C(O)—$C_{1-6}$alkyl. Preferably R¹ is —C(O)—$CH_2CH_3$.

DETAILED DESCRIPTION OF THE PREFERRED EMBODIMENT

The present invention is described in terms known and appreciated by those skilled in the art. For ease of reference certain terms hereafter are defined. The fact that certain terms are defined, however, should not be considered as indicative that defined terms are used in a manner necessarily inconsistent with the ordinary meaning or, alternatively, that any term that is undefined is indefinite or not used within the ordinary meaning. Rather, all terms used herein are believed to describe the invention such that one of ordinary skill can appreciate the scope of the present invention.

As used herein the term "alkyl" refers to a straight or branched chain hydrocarbon, preferably having from one to twelve carbon atoms, which may be optionally substituted. Examples of "alkyl" as used herein include, but are not limited to, methyl, ethyl, propyl, isopropyl, isobutyl, n-butyl, tert-butyl, isopentyl, n-pentyl, and the like.

As used herein the term "halogen" refers to fluorine, chlorine, bromine, or iodine.

As used herein the term "haloalkyl" refers to an alkyl group, as defined herein, that is substituted with at least one halogen. Examples of branched or straight chained "haloalkyl" groups useful in the present invention include, but are not limited to, methyl, ethyl, propyl, isopropyl, n-butyl, and t-butyl substituted independently with one or more halogens, for example, fluoro, chloro, bromo, and iodo. The term "haloalkyl" should be interpreted to include such groups as perfluoroalkyl groups and the like.

As used herein, the term "cycloalkyl" refers to a non-aromatic cyclic hydrocarbon ring, preferably having from three to ten carbon atoms, which may be optionally substituted. Exemplary "cycloalkyl" groups include, but are not limited to, cyclopropyl, cyclobutyl, cyclopentyl, cyclohexyl, and cycloheptyl.

As used herein, the term "aryl" refers to an optionally substituted benzene ring or to an optionally substituted benzene ring system fused to one or more optionally substituted benzene rings to form, for example, anthracene, phenanthrene, or naphthalene ring systems. Examples of "aryl" groups include, but are not limited to, phenyl, 2-naphthyl, 1-naphthyl, and biphenyl, as well as substituted derivatives thereof.

As used herein, the term "heteroaryl" refers to a monocyclic aromatic ring, or to a fused bicyclic aromatic ring system comprising two of such monocyclic aromatic rings, containing one or more heteroatom, such as one or more nitrogen, sulfur, and/or oxygen atoms, where N-oxides, sulfur oxides, and dioxides also are permissible heteroatom substitutions. The heteroaryl rings may be optionally substituted and multiple degrees of substitution should be considered within the scope of the present invention. Examples of "heteroaryl" groups used herein include, but should not be limited to, furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, indazole, and substituted versions thereof.

As used herein, the term "heterocycle" or "heterocyclyl" refers to a mono- or poly-cyclic ring system containing optionally one or more degrees of unsaturation and also containing one or more heteroatoms. Preferred heteroatoms include N, O, and/or S, including N-oxides, sulfur oxides, and dioxides. Preferably the ring is three to ten-membered and is either saturated or has one or more degrees of unsaturation. Optionally, as used herein, the heterocycle may be substituted, with multiple degrees of substitution being allowed. Such rings may be optionally fused to one or more of another "heterocyclic" ring(s), heteroaryl ring(s), aryl ring(s), or cycloalkyl ring(s). Examples of "heterocyclic" groups include, but are not limited to, tetrahydrofuran, pyran, 1,4-dioxane, 1,3-dioxane, piperidine, pyrrolidine, morpholine, tetrahydrothiopyran, and tetrahydrothiophene.

Also, as used herein throughout the present specification, the phrase "optionally substituted" or variations thereof denote an optional substitution, including multiple degrees of substitution, with one or more substitutent group. The phrase should not be interpreted as duplicative of the substitutions herein described and depicted. Exemplary optional substituent groups include acyl; alkyl; alkenyl; alkynyl; alkylsulfonyl; alkoxy; cyano; halogen; haloalkyl; hydroxy; nitro; cycloalkyl, which may be further substituted with acyl, alkoxy, alkyl, alkenyl, alkynyl, alkylsulfonyl, cyano, halogen, haloalkyl, hydroxy, or nitro; heterocyclyl, which may be further substituted with acyl, alkoxy, alkyl, alkenyl, alkynyl, alkylsulfonyl, cyano, halogen, haloalkyl, hydroxy, or nitro; aryl, which may be further substituted with acyl, alkoxy, alkyl, alkenyl, alkynyl, alkylsulfonyl, cyano, halogen, haloalkyl, hydroxy, or nitro; heteroaryl, which may be further substituted with acyl, alkoxy, alkyl, alkenyl, alkynyl, alkylsulfonyl, cyano, halogen, haloalkyl, hydroxy, or nitro; or —$CO_2H$.

The compounds of formulas (I) may crystallize in more than one form, a characteristic known as polymorphism, and such polymorphic forms ("polymorphs") are within the scope of formula (I). Polymorphism generally can occur as a response to changes in temperature, pressure, or both. Polymorphism can also result from variations in the crystallization process. Polymorphs can be distinguished by various physical characteristics known in the art such as x-ray diffraction patterns, solubility, and melting point.

Certain of the compounds described herein contain one or more chiral centers, or may otherwise be capable of existing as multiple stereoisomers. The scope of the present invention includes mixtures of stereoisomers as well as purified enantiomers or enantiomerically/diastereomerically enriched mixtures. Also included within the scope of the invention are the individual isomers of the compounds represented by formula (I), as well as any wholly or partially equilibrated mixtures thereof. The present invention also includes the individual isomers of the compounds represented by the formulas above as mixtures with isomers thereof in which one or more chiral centers are inverted.

Typically, the salts of the present invention are pharmaceutically acceptable salts. Salts encompassed within the term "pharmaceutically acceptable salts" refer to non-toxic salts of the compounds of this invention. Salts of the compounds of the present invention may comprise acid addition salts. Representative salts include acetate, benzenesulfonate, benzoate, bicarbonate, bisulfate, bitartrate, borate, bromide, calcium, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, magnesium, malate, maleate, mandelate, mesylate, methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, sulfate, tannate, tartrate, teoclate, tosylate, triethiodide, trimethylammonium, valerate, and zinc salts. Other salts, which are not considered as pharmaceutically acceptable, may be useful in manufacture and these should be considered to form a further aspect of the invention.

As used herein, the term "solvate" refers to a complex of variable stoichiometry formed by a solute (in this invention, a compound of Formula I, or a salt or physiologically functional derivative thereof) and a solvent. Such solvents, for the purpose of the invention, should not interfere with the biological activity of the solute. Non-limiting examples of suitable solvents include, but are not limited to water, methanol, ethanol, and acetic acid. Preferably the solvent used is a pharmaceutically acceptable solvent. Non-limiting examples of suitable pharmaceutically acceptable solvents include water, ethanol, and acetic acid. Most preferably the solvent used is water.

As used herein, the term "physiologically functional derivative" refers to any pharmaceutically acceptable derivative of a compound of the present invention that, upon administration to a mammal, is capable of providing (directly or indirectly) a compound of the present invention or an active metabolite thereof. Reference may be made to the teaching of *Burger's Medicinal Chemistry And Drug Discovery*, $5^{th}$ Edition, Vol 1: Principles and Practice, which is incorporated herein by reference to the extent that it teaches physiologically functional derivatives.

As used herein, the term "effective amount" means that amount of a drug or pharmaceutical agent that will elicit the biological or medical response of a tissue, system, animal or human that is being sought, for instance, by a researcher or clinician. The term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

For use in therapy, therapeutically effective amounts of a compound of formula (I), as well as salts, solvates, and physiological functional derivatives thereof, may be administered as the raw chemical. Additionally, the active ingredient may be presented as a pharmaceutical composition. Accordingly, the invention further provides pharmaceutical compositions that include effective amounts of compounds of the formula (I) and salts, solvates, and physiological functional derivatives thereof, and one or more pharmaceutically acceptable carriers, diluents, or excipients. The compounds of formula (I) and salts, solvates, and physiologically functional derivatives thereof, are as described above. The carrier(s), diluent(s) or excipient(s) must be acceptable, in the sense of being compatible with the other ingredients of the formulation and not deleterious to the recipient of the pharmaceutical composition. In accordance with another aspect of the invention there is also provided a process for the preparation of a pharmaceutical formulation including admixing a compound of the formula (I) or salts, solvates, and physiological functional derivatives thereof, with one or more pharmaceutically acceptable carriers, diluents or excipients.

A therapeutically effective amount of a compound of the present invention will depend upon a number of factors. For example, the age and weight of the animal, the precise condition requiring treatment and its severity, the nature of the formulation, and the route of administration are all factors to be considered. The therapeutically effective amount ultimately should be at the discretion of the attendant physician or veterinarian. For example, an effective amount of a compound of formula (I) for the treatment of humans suffering from osteoporosis, generally, should be in the range of 0.1 to 100 mg/kg body weight of recipient (mammal) per day. More usually the effective amount should be in the range of 1 to 10 mg/kg body weight per day. Thus, for a 70 kg adult mammal the actual amount per day would usually be from 70 to 700 mg. This amount may be given in a single dose per day or in a number (such as two, three, four, five, or more) of sub-doses per day such that the total daily dose is the same. An effective amount of a salt, solvate, or physiologically functional derivative thereof, may be determined as a proportion of the effective amount of the compound of formula (I) per se. Similar dosages should be appropriate for treatment of the other conditions referred to herein that are mediated by estrogen.

Pharmaceutical formulations may be presented in unit dose forms containing a predetermined amount of active ingredient per unit dose. Such a unit may contain, as a non-limiting example, 0.5 mg to 1 g of a compound of the formula (I), depending on the condition being treated, the route of administration, and the age, weight, and condition of the patient. Preferred unit dosage formulations are those containing a daily dose or sub-dose, as herein above recited, or an appropriate fraction thereof, of an active ingredient. Such pharmaceutical formulations may be prepared by any of the methods well known in the pharmacy art.

Pharmaceutical formulations may be adapted for administration by any appropriate route, for example by an oral (including buccal or sublingual), rectal, nasal, topical (including buccal, sublingual or transdermal), vaginal, or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions, each with aqueous or non-aqueous liquids; edible foams or whips; or oil-in-water liquid emulsions or water-in-oil liquid emulsions. For instance, for oral administration in the form of a tablet or capsule, the active drug component can be combined with an oral, non-toxic pharmaceutically acceptable inert carrier such as ethanol, glycerol, water, and the like. Generally, powders are prepared by comminuting the compound to a suitable fine size and mixing with an appropriate pharmaceutical carrier such as an edible carbohydrate, as, for example, starch or mannitol. Flavorings, preservatives, dispersing agents, and coloring agents can also be present.

Capsules are made by preparing a powder, liquid, or suspension mixture and encapsulating with gelatin or some other appropriate shell material. Glidants and lubricants such as colloidal silica, talc, magnesium stearate, calcium stearate or solid polyethylene glycol can be added to the mixture before the encapsulation. A disintegrating or solubilizing agent such as agar-agar, calcium carbonate or sodium carbonate can also be added to improve the availability of the medicament when the capsule is ingested. Moreover, when desired or necessary, suitable binders, lubricants, disintegrating agents, and coloring agents can also be incorporated into the mixture. Examples of suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes, and the like. Lubricants useful in these dosage forms include, for example, sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like. Tablets are formulated, for example, by preparing a powder mixture, granulating or slugging, adding a lubricant and disintegrant, and pressing into tablets. A powder mixture may be prepared by mixing the compound, suitably comminuted, with a diluent or base as described above. Optional ingredients include binders, such as carboxymethylcellulose, aliginates, gelatins, or polyvinyl pyrrolidone, solution retardants, such as paraffin, resorption accelerators such as a quaternary salt and/or absorption agents such as bentonite, kaolin, or dicalcium phosphate. The powder mixture can be wet-granulated with a binder such as syrup, starch paste, acadia mucilage or solutions of cellulosic or polymeric materials, and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solutions, syrups, and elixirs can be prepared in dosage unit form so that a given quantity contains a predetermined amount of the compound. Syrups can be prepared, for example, by dissolving the compound in a suitably flavored aqueous solution, while elixirs are prepared through the use of a non-toxic alcoholic vehicle. Suspensions can be formulated generally by dispersing the compound in a non-toxic vehicle. Solubilizers and emulsifiers such as ethoxylated isostearyl alcohols and polyoxy ethylene sorbitol ethers, preservatives; flavor additives such as peppermint oil, or natural sweeteners, saccharin, or other artificial sweeteners; and the like can also be added.

Where appropriate, dosage unit formulations for oral administration can be microencapsulated. The formulation can also be prepared to prolong or sustain the release as for example by coating or embedding particulate material in polymers, wax or the like.

The compounds of formula (I) and salts, solvates, and physiological functional derivatives thereof, can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

The compounds of formula (I) and salts, solvates, and physiologically functional derivatives thereof may also be delivered by the use of monoclonal antibodies as individual carriers to which the compound molecules are coupled. The compounds may also be coupled with soluble polymers as targetable drug carriers. Such polymers can include polyvinylpyrrolidone (PVP), pyran copolymer, polyhydroxypropylmethacrylamide phenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug; for example, polylactic acid, polyepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research,* 3(6), 318 (1986), incorporated herein by reference as related to such delivery systems.

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations may be applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical formulations adapted for topical administrations to the eye include eye drops wherein the active ingredient is dissolved or suspended in a suitable carrier, especially an aqueous solvent. Pharmaceutical formulations adapted for topical administration in the mouth include lozenges, pastilles, and mouthwashes.

Pharmaceutical formulations adapted for nasal administration, where the carrier is a solid, include a coarse powder having a particle size for example in the range 20 to 500 microns. The powder is administered in the manner in which snuff is taken, i.e., by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for rectal administration may be presented as suppositories or as enemas.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and solutes that render the formulation isotonic with the blood of the intended recipient; and aqueous and non-aqueous sterile suspensions which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

In addition to the ingredients particularly mentioned above, the formulations may include other agents conventional in the art having regard to the type of formulation in question. For example, formulations suitable for oral administration may include flavoring agents.

The compounds of the present invention and their salts, solvates, and physiologically functional derivatives thereof, may be employed alone or in combination with other therapeutic agents for the treatment of the conditions herein described. For example, in osteoporosis therapy, combination with other osteoporosis therapeutic agents is envisaged. Osteoporosis combination therapies according to the present invention thus comprise the administration of at least one compound of formula (I) or a salt, solvate, or physiologically functional derivative thereof, and the use of at least one other osteoporosis treatment method. Preferably, combination therapies according to the present invention comprise the administration of at least one compound of formula (I) or a salt, solvate, or physiologically functional derivative thereof, and at least one other osteoporosis treatment agent, for example, a bone building agent. The compound(s) of formula (I) and the other pharmaceutically active agent(s) may be administered together or separately and, when administered separately, administration may occur simultaneously or sequentially in any order. The amounts of the compound(s) of formula (I) and the other pharmaceutically active agent(s) and the relative timings of administration will be selected in order to achieve the desired combined therapeutic effect. The administration in combination of a compound of formula (I) salts, solvates, or physiologically functional derivatives thereof with other osteoporosis treatment agents may be in combination by administration concomitantly in: (1) a unitary pharmaceutical composition including each compound; or (2) separate pharmaceutical compositions each including one of the compounds. Alternatively, the combination may be administered separately in a sequential manner wherein one treatment agent is administered first and the other(s) subsequently or vice versa. Such sequential administration may be close in time or remote in time.

The compounds of the present invention and their salts, solvates, and physiologically functional derivatives thereof, may be employed alone or in combination with other therapeutic agents for the treatment of the conditions herein described. For example, regarding the use of the compounds of the present invention in the prevention of reduced bone mass, density, or growth, combination may be had with other anabolic or osteoporosis therapeutic agents. As one example, osteoporosis combination therapies according to the present invention would thus comprise the administration of at least one compound of the present invention or a salt, solvate, or physiologically functional derivative thereof, and the use of at least one other osteoporosis therapy. As a further example, combination therapies according to the present invention include the administration of at least one compound of the present invention or a salt, solvate, or physiologically functional derivative thereof, and at least one other osteoporosis treatment agent, for example, an anti-bone resorption agent. The compound(s) of the present invention and the other pharmaceutically active agent(s) may be administered together or separately and, when administered separately, administration may occur simultaneously or sequentially, in any order. The amounts of the compound(s) and the agent(s) and the relative timings of administration will be selected in order to achieve the desired combined therapeutic effect. The administration in combination of a compound of the present invention including salts, solvates, or physiologically functional derivatives thereof with other treatment agents may be in combination by administration concomitantly in: (1) a unitary pharmaceutical composition including both compounds; or (2) separate pharmaceutical compositions each including one of the compounds. Alternatively, the combination may be administered separately in a sequential manner wherein one treatment agent is administered first and the other second or vice versa. Such sequential administration may be close in time or remote in time.

As noted, one potential additional osteoporosis treatment agent is a bone building (anabolic) agent. Bone building agents can lead to increases in parameters such as bone mineral density that are greater than those than can be achieved with anti-resorptive agents. In some cases, such anabolic agents can increase trabecular connectivity leading to greater structural integrity of the bone.

Other potential therapeutic combinations include the compounds of the present invention combined with other compounds of the present invention, growth promoting agents, growth hormone secretagogues, growth hormone releasing factor and its analogs, growth hormone and its analogs, somatomedins, alpha-ardenergic agonists, serotonin $5-HT_D$ agonists, selective serotonin reuptake inhibitors, agents that inhibit somatostatin or its release, 5-α-reductase inhibitors, aromatase inhibitors, GnRH inhibitors, parathyroid hormone, bisphosphonates, estrogen, testosterone, SERMs, progesterone receptor agonists, and/or with other modulators of nuclear hormone receptors.

The compounds of the present invention may be used in the treatment of a variety of disorders and conditions and, as such, the compounds of the present invention may be used in combination with a variety of other suitable therapeutic agents useful in the treatment or prophylaxis of those disorders or conditions. Non-limiting examples include combinations of the present invention with anti-diabetic agents, anti-osteoporosis agents, anti-obesity agents, anti-inflammatory agents, anti-anxiety agents, anti-depressants, anti-hypertensive agents, anti-platelet agents, anti-thrombotic and thrombolytic agents, cardiac glycosides, cholesterol or lipid lowering agents, mineralocorticoid receptor antagonists, phosphodiesterase inhibitors, kinase inhibitors, thyroid mimetics, anabolic agents, viral therapies, cognitive disorder therapies, sleeping disorder therapies, sexual dysfunction therapies, contraceptives, cytotoxic agents, radiation therapy, anti-proliferative agents, and anti-tumor agents. Additionally, the compounds of the present invention may be combined with nutritional supplements such as amino acids, triglycerides, vitamins, minerals, creatine, piloic acid, carnitine, or coenzyme Q10.

An aspect of the present invention is the use of the compounds of the present invention for the treatment or prophylaxis of a variety of disorders including, but not limited to, osteoporosis, bone demineralization and/or the prevention of reduced bone mass, density, or growth, osteoarthritis, acceleration of bone fracture repair and healing, acceleration of healing in joint replacement, periodontal disease, acceleration of tooth repair or growth, Paget's disease, osteochondrodysplasias, muscle wasting, the maintenance and enhancement of muscle strength and function, frailty or age-related functional decline ("ARFD"), sarcopenia, chronic fatigue syndrome, chronic myalgia, acute fatigue syndrome, acceleration of wound healing, maintenance of sensory function, chronic liver disease, AIDS, weightlessness, burn and trauma recovery, thrombocytopenia, short bowel syndrome, irritable bowel syndrome, inflammatory bowel disease, Crohn's disease and ulcerative colitis, obesity, eating disorders including anorexia associated with cachexia or aging, hypercortisolism and Cushing's syndrome, cardiovascular disease or cardiac dysfunction, congestive heart failure, high blood pressure, breast cancer, malignant tumor cells including breast, brain, skin, ovary, bladder, lymphatic, liver, kidney, uterine, pancreas, endometrium, lung, colon, and prostate, prostatic hyperplasia, hirsutism, acne, seborrhea, androgenic alopecia, anemia, hyperpilosity, adenomas and neoplasis of the prostate, hyperinsulinemia, insulin resistance, diabetes, syndrome X, dyslipidemia, urinary incontinence, artherosclerosis, libido enhancement, sexual dysfunction, depression, depressive symptoms, nervousness, irritability, stress, reduced mental energy and low self-esteem, improvement of cognitive function, endometriosis, polycystic ovary syndrome, counteracting preeclampsia, premenstral syndrome, contraception, uterine fibroid disease, and/or aortic smooth muscle cell proliferation, vaginal dryness, pruritis, dyspareunia, dysuria, frequent urination, urinary tract infections, hypercholesterolemia, hyperlipidemia, peripheral vascular disease, restenosis, vasospasm, vascular wall damage due to immune responses, Alzheimer's disease, bone disease, aging, inflammation, rheumatoid arthritis, respiratory disease, emphysema, reperfusion injury, viral hepatitis, tuberculosis, psoriasis, amyotrophic lateral sclerosis, stroke, CNS trauma, dementia, neurodegeneration, breast pain and dysmenorrhea, menopausal or postmenopausal disorders, vasomotor symptoms, urogenital or vulvar vaginal atrophy, atrophic vaginitis, female sexual dysfunction, for enhancing libido, for the treatment of hypoactive sexual disorder, sexual arousal disorder, for increasing the frequency and intensity of orgasms, vaginismus, osteopenia, endometriosis, BPH (benign prostatic hypertrophy), autoimmune diseases, Hashimoto's thyroiditis, SLE (systemic lupus erythematosus), myasthenia gravis, reperfusion damage of ischemic myocardium, In particular, the compounds of the present invention are believed useful, either alone or in combination with other agents, in the treatment of menopausal or postmenopausal disorders, vasomotor symptoms, urogenital or vulvar vaginal atrophy, atrophic vaginitis, female sexual dysfunction, breast cancer, depressive symptoms, diabetes, bone demineralization, and the treatment and/or prevention of osteoporosis.

The compounds of this invention may be made by a variety of methods. Illustrative general synthetic methods are set out below and then specific compounds of the invention are prepared in the working Examples.

In all of the examples described below, protecting groups for sensitive or reactive groups are employed where necessary in accordance with general principles of synthetic chemistry. Protecting groups are manipulated according to standard methods of organic synthesis (T. W. Green and P. G. M. Wuts (1991) *Protecting Groups in Organic Synthesis*, John Wiley & Sons, incorporated by reference with regard to protecting groups). These groups are removed at a convenient stage of the compound synthesis using methods that are readily apparent to those skilled in the art. The selection of processes as well as the reaction conditions and order of their execution shall be consistent with the preparation of compounds of formula (I).

Those skilled in the art will recognize if a stereocenter exists in compounds of formula (I). Accordingly, the present invention includes all possible stereoisomers and includes not only racemic compounds but the individual enantiomers as well. When a compound is desired as a single enantiomer, such may be obtained by stereospecific synthesis, by resolution of the final product or any convenient intermediate, or by chiral chromatographic methods as are known in the art. Resolution of the final product, an intermediate, or a starting material may be effected by any suitable method known in the art. See, for example, *Stereochemistry of Organic Compounds* by E. L. Eliel, S. H. Wilen, and L. N. Mander (Wiley-Interscience, 1994), incorporated by reference with regard to stereochemistry.

EXPERIMENTAL SECTION

Abbreviations:

As used herein the symbols and conventions used in these processes, schemes and examples are consistent with those used in the contemporary scientific literature, for example, the *Journal of the American Chemical Society or the Journal of Biological Chemistry*. Specifically, the following abbreviations may be used in the examples and throughout the specification:

g (grams); mg (milligrams);
L (liters); mL (milliliters);
M (molar); mM (millimolar);
Hz (Hertz); MHz (megahertz);
mol (moles); mmol (millimoles);
RT (room temperature); h (hours);
min (minutes); TLC (thin layer chromatography);
mp (melting point); RP (reverse phase);
$T_r$ (retention time); d (days);
mm (millimeter) $SiO_2$ (silica);
TFA (trifluoroacetic acid); LiCl (lithium chloride)
$Et_3N$ (triethylamine); THF (tetrahydrofuran);
TFAA (trifluoroacetic anhydride); $CD_3OD$ (deuterated methanol);
$CDCl_3$ (deuterated chloroform); DMSO (dimethylsulfoxide);
EtOAc (ethyl acetate); $CHCl_3$ (chloroform);
HCl (hydrochloric acid); Ac (acetyl);
DMF (N,N-dimethylformamide); Me (methyl);
$Cs_2CO_3$ (cesium carbonate); EtOH (ethanol);
t-BuOH (tert-butyl alcohol) i-PrOH (isopropyl alcohol)
Et (ethyl); tBu (tert-butyl);
MeOH (methanol); $CH_2Cl_2$ (dichloromethane);
$MgSO_4$ (magnesium sulfate); $CH_3CN$ (acetonitrile);
$K_2CO_3$ (potassium carbonate); EtOAc (ethyl acetate);
$POCl_3$ (phosphorous oxychloride); $Et_2O$ (diethyl ether);
$Na_2SO_4$ (sodium sulfate); nBuLi (butyllithium);
NaH (sodium hydride); NaI (sodium iodide);
NaOH (sodium hydroxide); $BBr_3$ (boron tribromide);
$NH_4Cl$ (ammonium chloride); $NaHCO_3$ (sodium bicarbonate);
$AlCl_3$ (aluminum chloride); $CaCl_2$ (calcium chloride);
MTBE (methyl tert-butyl ether);
DBU (1,8-diazabicyclo[5.4.0]undecene);
LCMS (liquid chromatography mass spectrometry);
HPLC (high performance liquid chromatography);

Unless otherwise noted, reagents and solvents were obtained from commercial suppliers and were used without further purification. Unless otherwise indicated, all reactions were conducted at room temperature and all temperatures are expressed in ° C. (degrees Centigrade).

Thin-layer chromatography (TLC) was performed on silica gel 60 $F_{254}$ precoated plates. Detection was effected by exposure to UV light (254 nm). Flash and flush column chromatography was performed using Silica Gel 60. Reverse phase preparative and analytical HPLC were performed using C18 columns and $CH_3CN:H_2O$ gradients with 0.1% TFA as a modifier.

Compound purity and characterization were determined by $^1$H-NMR, liquid chromatography-mass spectrometry (LCMS), combustion (elemental) analysis, HPLC, and melting point. Compounds of general formula I were typically found to have purities of >90%.

$^1$H NMR spectra were recorded on Varian INOVA-300 and Varian INOVA-400 instruments. $^{31}$PNMR spectra were recorded. Chemical shifts are expressed in parts per million (ppm, δ units). Coupling constants are in units of hertz (Hz). Splitting patterns describe apparent multiplicities and are designated as s (singlet), d (doublet), dd (doublet of doublet), t (triplet), q (quartet), h (heptet), m (multiplet), or br (broad).

Low resolution mass spectra (MS) were obtained on Micromass ZQ, Micromass ZMD, Micromass QuattroMicro, and Micromass GCT instruments from Micromass Ltd., Altricham, UK, using either Atmospheric Pressure Chemical Ionization (APCI) or Electrospray Ionization (ESI).

Combustion analyses were performed by Atlantic Microlab, Inc. (Norcross, Ga.).

Melting points were recorded in open capillary tubes and are uncorrected.

The bolded numerals reference the compounds as depicted in the following schemes. The compounds of Formula I were prepared according to representative Schemes 1-9, which are below presented. The compounds, which may be prepared according to these schemes, should not be limited by the exemplary compounds contained in the schemes or by any particular substituents exemplified in the schemes. Rather, all should be considered as illustrative.

A selective synthesis of (2E)-3-{4-[(1Z)-1-(4-hydroxyphenyl)-2-phenylbut-1-enyl]phenyl}prop-2-enoic acid (1) (also referred to as Z-7604) has not been reported. Rather, Weatherman (*Chem. and Biol.* (2001) 8, 427-436) isolated this material (characterized therein as the "undesired Z isomer") by fractional crystallization of a mixture of the E and Z-isomers. Weatherman (Id.) reported a binding affinity for 1 to the estrogen receptor subtypes alpha and beta be 2% and 1% that of estradiol, respectively.

As herein described, compound 1 can be prepared as illustrated in Scheme 1. Friedel-Crafts acylation between 2-phenylbutanoyl chloride (II) and anisole provides the aryl ketone 2.

Scheme 1. Preparation of Compound 1

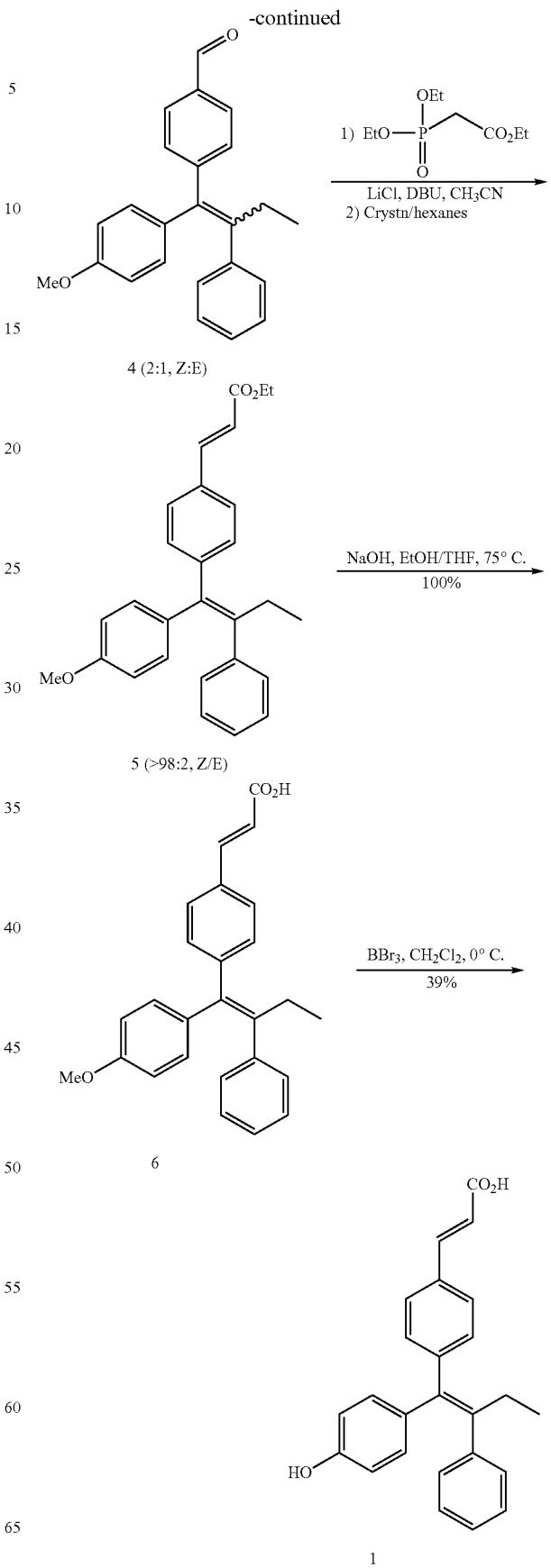

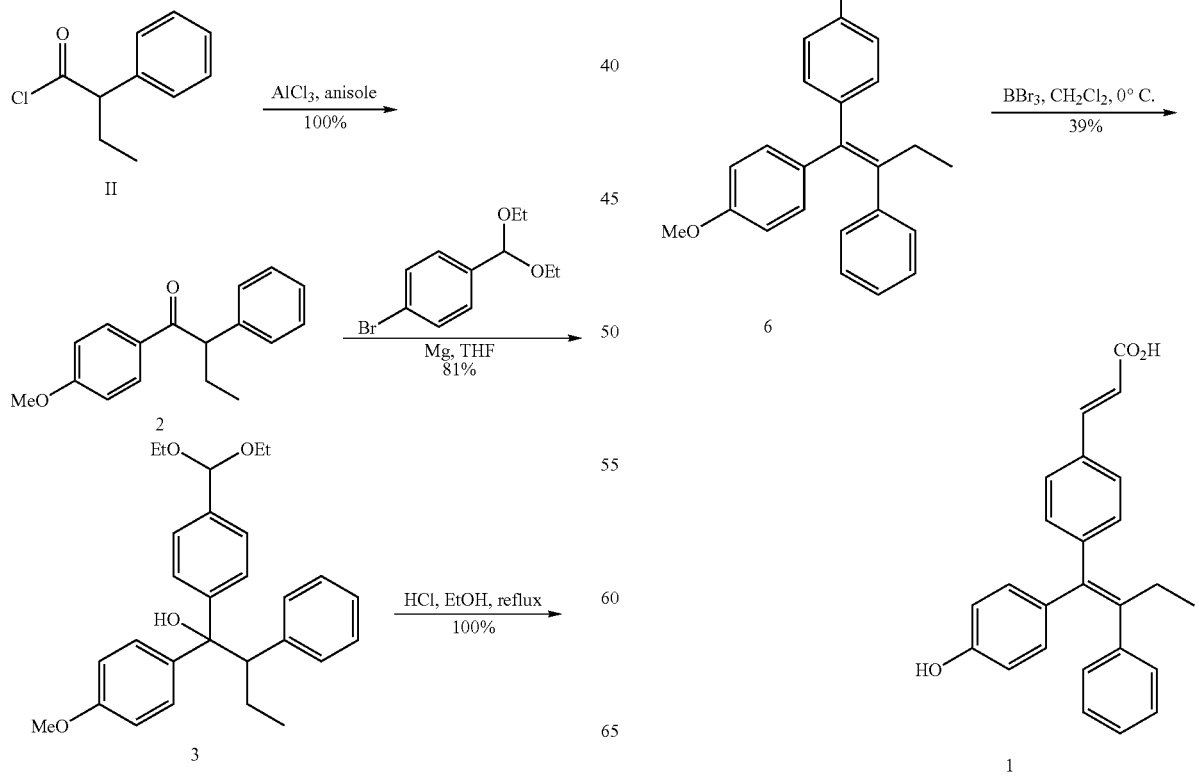

For Friedel-Crafts reaction conditions, see *Friedel-Crafts and Related Reactions*, G. A. Olah, ed., Vol 3, Pt 1, pp 1-382, J. Wiley and Sons, New York (1964); G. A. Olah, *Friedel-Crafts Chemistry*, Wiley Interscience, New York, (1973); and Larock, R. C., *Comprehensive Organic Transformations*, VCH Publishers, New York, 1989, each herein incorporated by reference with regard to such teaching. Addition of the Grignard reagent of 1-bromo-4-(diethoxymethyl)benzene to aryl ketone 2 provided the tertiary carbinol 3 which was subsequently dehydrated following treatment with hydrochloric acid to furnish the aldehyde 4 as a 2:1 Z:E isomeric mixture (For a definition of Z and E isomers see: *Pure Appl. Chem.* (1976) 45, 13, herein incorporated by reference). Condensation of ethyl (diethoxyphosphoryl)acetate with aldehyde 4 using conditions described by Wadsworth and Emmons (Wadsworth and Emmons, *Org. Syn.* (1965), 45, 44, herein incorporated by reference) yielded ethyl ester 5. Saponification of 5 with NaOH/EtOH afforded the carboxylic acid 6. Conversion of 6 to 1 was effected by treatment with BBr$_3$.

As described in further detail below, despite being previously reported as an undesired by-product, compound 1 exhibits an apposite pKi against ER-α and ER-β. As noted, however, compound 1 does not have the appropriate characteristics for a commercializable pharmaceutical agent. For example, compound 1 is only poorly bioavailable. The prodrugs of 1 described herein overcome the deficiencies of the parent 1 and provide a suitable pharmaceutical profile.

The prodrugs described herein were prepared by several methods as described in the Schemes below. Ester prodrugs may be prepared as described in Scheme 2 (Method A) starting from 2-phenylbutanoic acid (III). Friedel-Crafts acylation of anisole with III (Ace, K. W., *Org. Proc. Res. & Dev.* (2001) 5, 479, herein incorporated by reference) followed by removal of the methyl ether with AlCl$_3$ yielded phenol 8. Following protection of the phenol group of 8 as a THP ether (Bandgar, *Monatsh. Chem.* (2003) 134, 425-428, herein incorporated by reference), wherein preferred reagents include an appropriate acid with an appropriate solvent, such as p-TSOH with CH$_2$Cl$_2$, CaCl$_2$ with CH$_2$Cl$_2$ or EDC, or anhydrous HCl with heptane, compound 9 was treated with [4-(dialkoxymethyl)phenyl]lithium (generated from 1-bromo-4-(dialkoxymethyl)benzene, such as the dimethylacetal or diethylacetal of 4-bromobenzaldehyde, and nBuLi) followed by acid catalyzed dehydration to afford the phenol aldehyde 10. The ester intermediates IV were prepared by acylation of 10 with an anhydride or acid chloride in the presence of a tertiary amine base such as Et$_3$N. The acrylic acid V was generated using standard Knoevenagel reaction conditions (G. Jones, *Org. Reactions* (1967) 15, 204, herein incorporated by reference).

Scheme 2. Preparation of Ester Prodrugs of Compound 1 - Method A

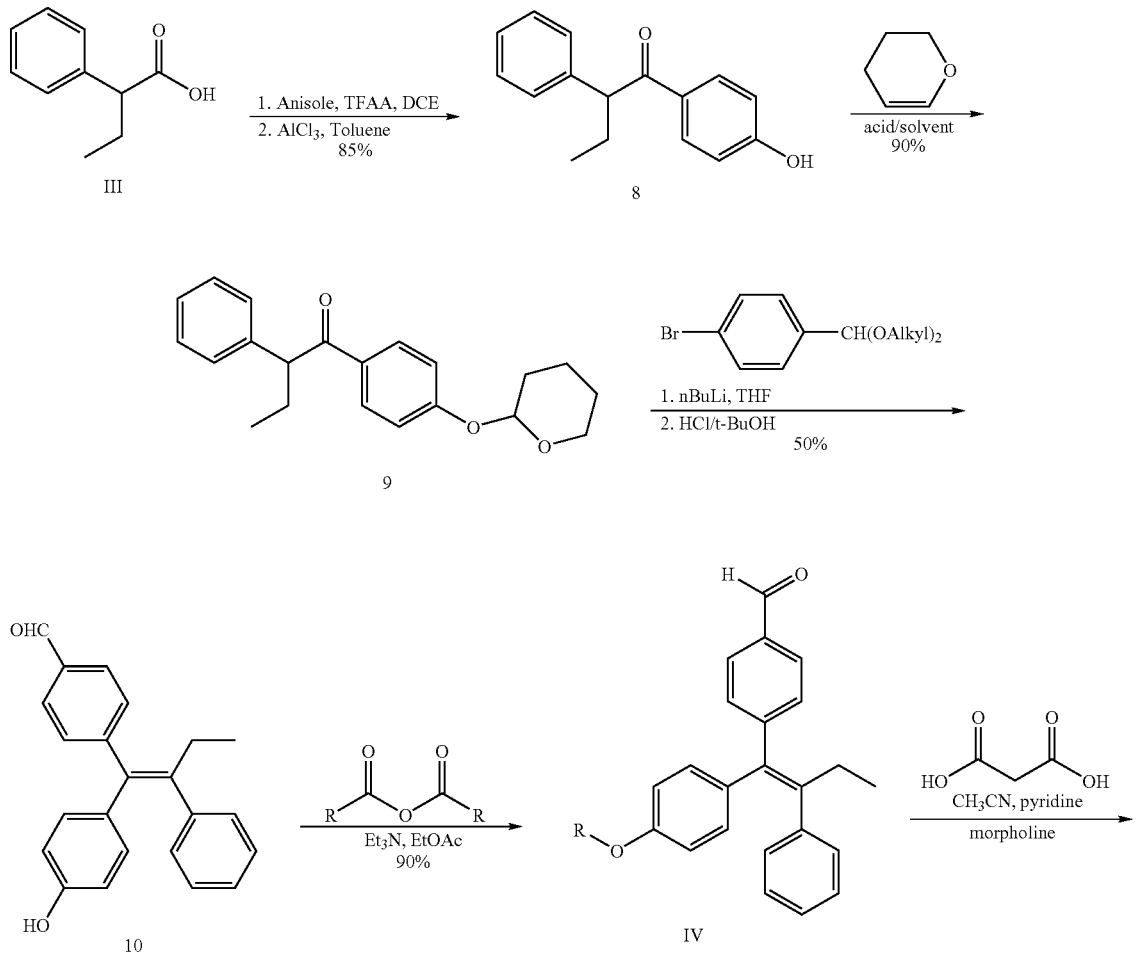

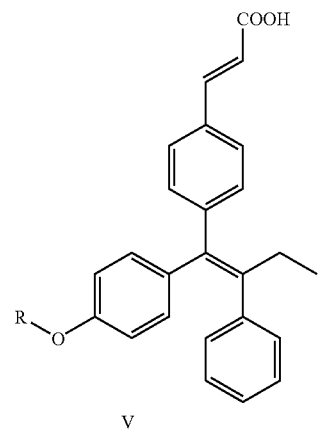

V

As illustrated in Scheme 2a, the phenol aldehyde 10 alternatively may be converted to the compound 1 using malonic acid, pyridine, and a catalytic amount of morpholine, as described above (G. Jones, *Org. Reactions* (1967) 15, 204, herein incorporated by reference):

Scheme 2a

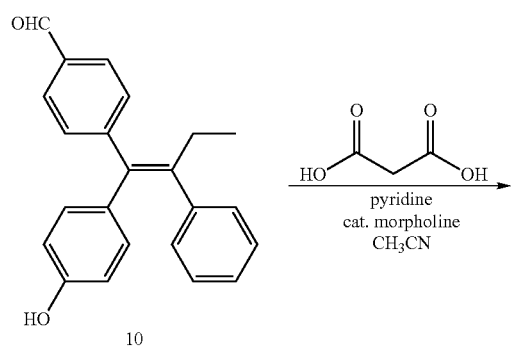

compound 1

Prodrugs were also prepared by acylation of 1 as described in Scheme 3 (Method B). The intermediate anhydride VI was decomposed by treatment with aqueous base to yield phenol esters V.

Scheme 3. Preparation of Ester Prodrugs of Compound 1 - Method B

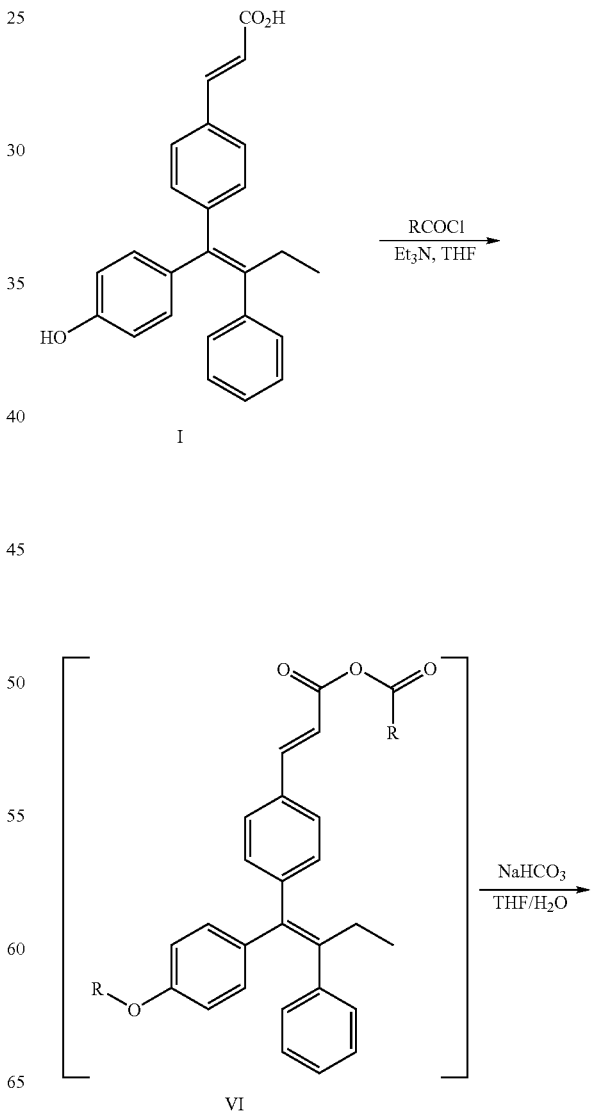

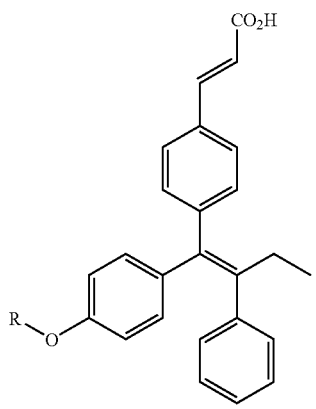

V

As shown in Scheme 4, ester prodrugs V were also be prepared via acylation of the tert-butyl ester 12, followed by removal of the tert-butyl group by treatment with trifluoroacetic acid (TFA) in $CH_2Cl_2$ (Greene, T. in *Protective Groups in Organic Synthesis*; Wiley Interscience: New York, (1981), p. 168, herein incorporated by reference as noted). The acylation reactions in Scheme 4 are typically performed in an aprotic solvent such as THF, $CH_3CN$, DMF or a chlorinated solvent such as $CH_2Cl_2$ or $CHCl_3$. In addition, the presence of a compound capable of acting as a base such as $Et_3N$, pyridine or $NaHCO_3$ is preferred in order to obtain sufficient yields of the coupling products.

Scheme 4. Preparation of Ester Prodrugs of Compound 1 - Method C

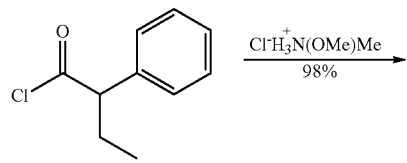

VII

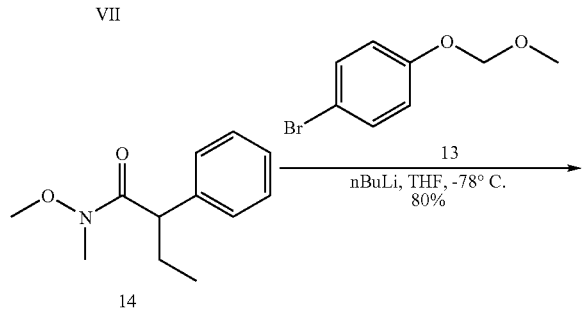

14

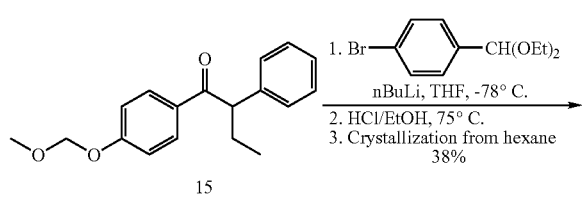

15

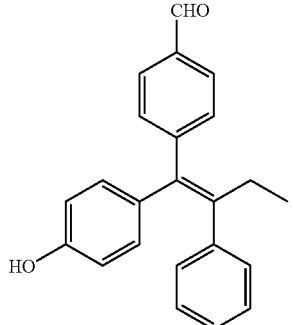

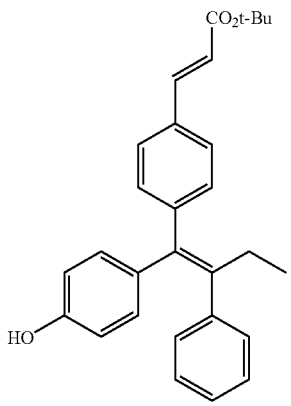

12
(9:1 Z:E)

V

Ester prodrugs V were also prepared from 1 via a two step procedure (Scheme 5) involving acylation of an intermediate silyl ester (30) following decomposition upon aqueous workup. The use of silyl esters as protecting groups has been described (Greene, T. in *Protective Groups in Organic Synthesis*; Wiley Interscience: New York, (1981), p. 179, herein incorporated by reference as noted)

Scheme 5. Preparation of Ester Prodrugs of Compound 1 - Method D

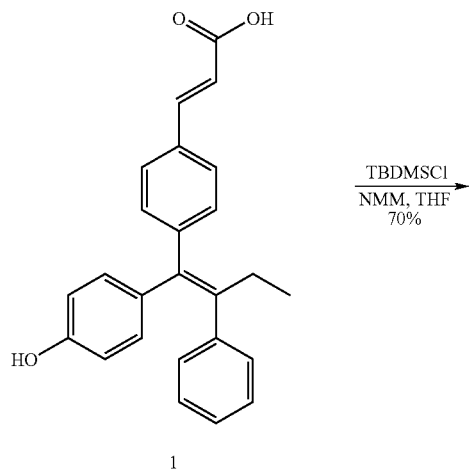

1

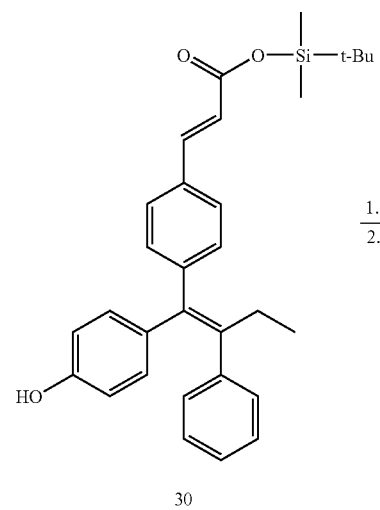

30

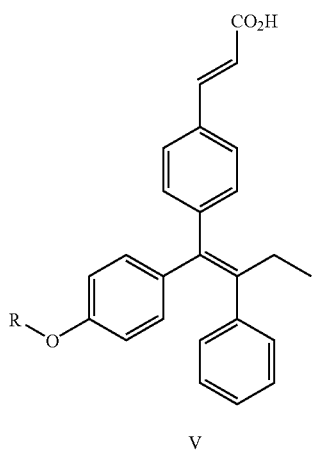

V

Scheme 6. Preparation of Substituted Glycine Ester Prodrugs

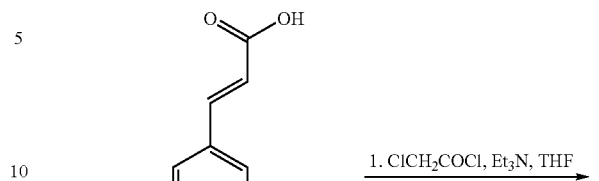

1

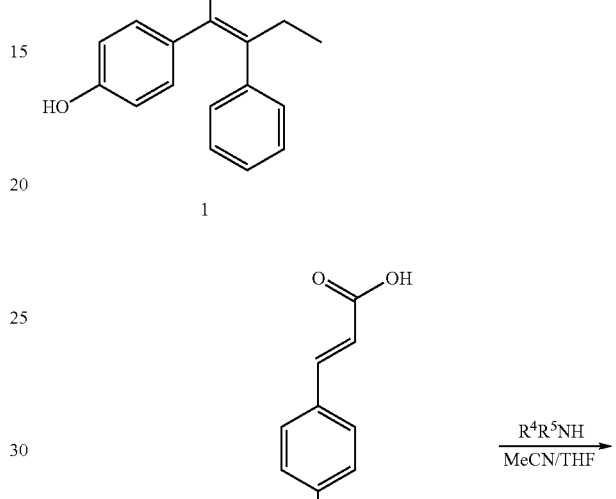

32

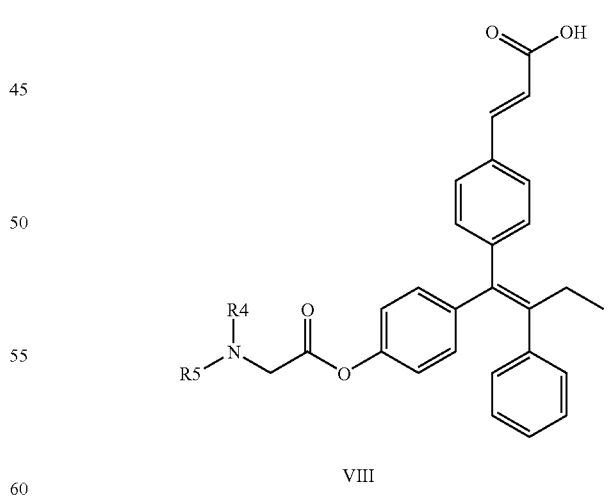

VIII

Substituted glycine-derived ester prodrugs VIII were prepared from 1 according to the methods described in Scheme 6. Acylation of 1 with chloroacetyl chloride afforded the α-haloester 32. The desired prodrugs VIII were generated by reaction of compound 32 with a secondary amine in the presence of NaI.

A phosphate prodrug of 1 was prepared as described in Scheme 7. Treatment of t-butyl ester 12 with $POCl_3$ followed by aqueous hydrolysis afforded the intermediate ester phosphate 36. Acidolysis of intermediate 36 with TFA as described previously yielded the desired phosphate prodrug 35.

Scheme 7. Preparation of a Phosphate Prodrug of Compound 1

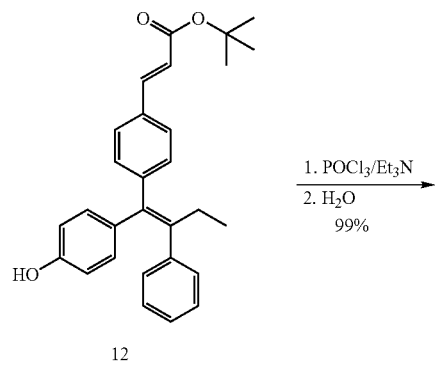

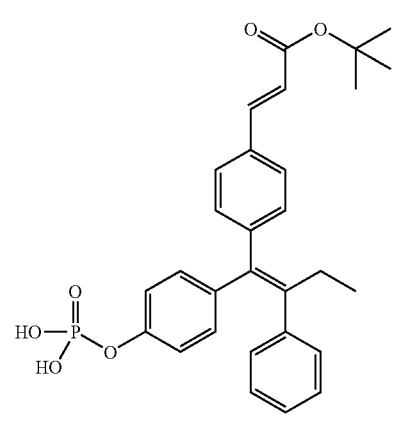

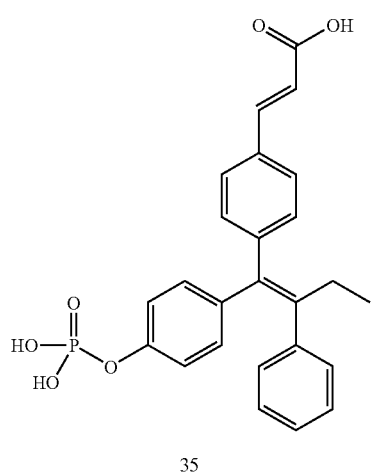

Scheme 8. Preparation of Carbonate Prodrugs of Compound 1 (Method A)

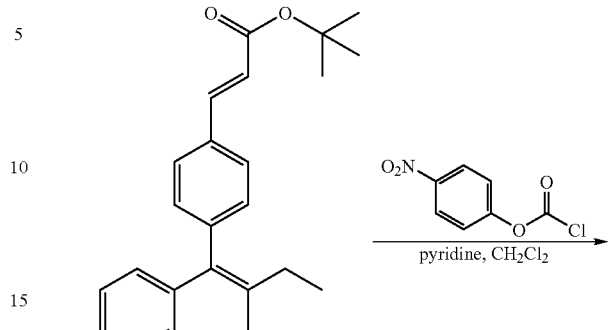

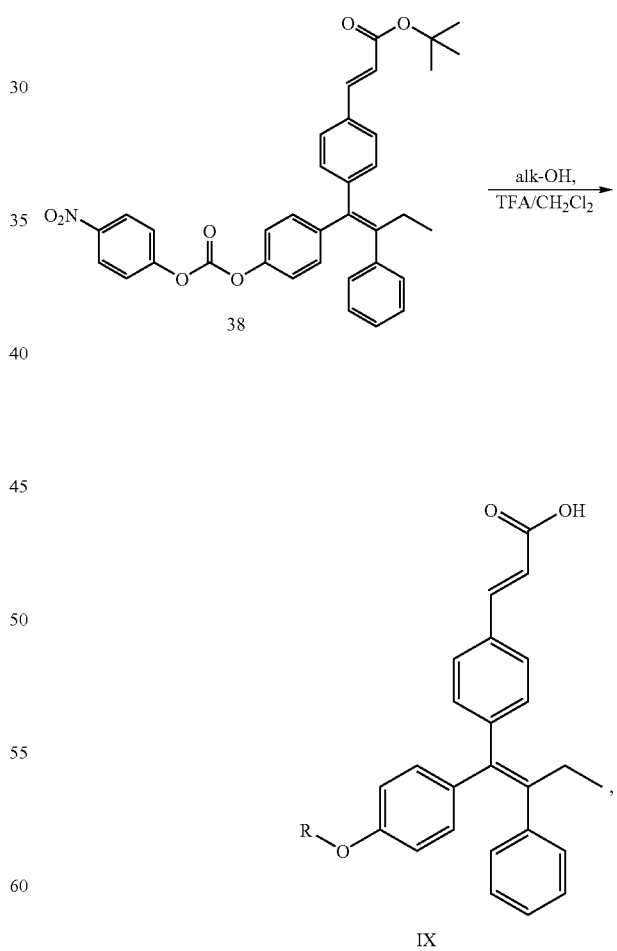

where R = —C(O)—O-alkyl

Certain substituted carbonate prodrugs IX were prepared from 1 as shown in Scheme 8. Reaction of the p-nitrophenylester intermediate 38 with an alcohol in the presence of a suitable tertiary amine base such as $Et_3N$, followed by standard removal of the t-butyl ester with TFA yield IX.

Alternatively, carbonate prodrugs of 1 were prepared, as described in Scheme 9, by reaction of 12 with an alkyl or arylchloroformate in the presence Et₃N, followed by standard removal of the t-butyl ester with TFA to yield IX.

Scheme 9. Preparation of Carbonate Prodrugs of Compound 1 (Method B)

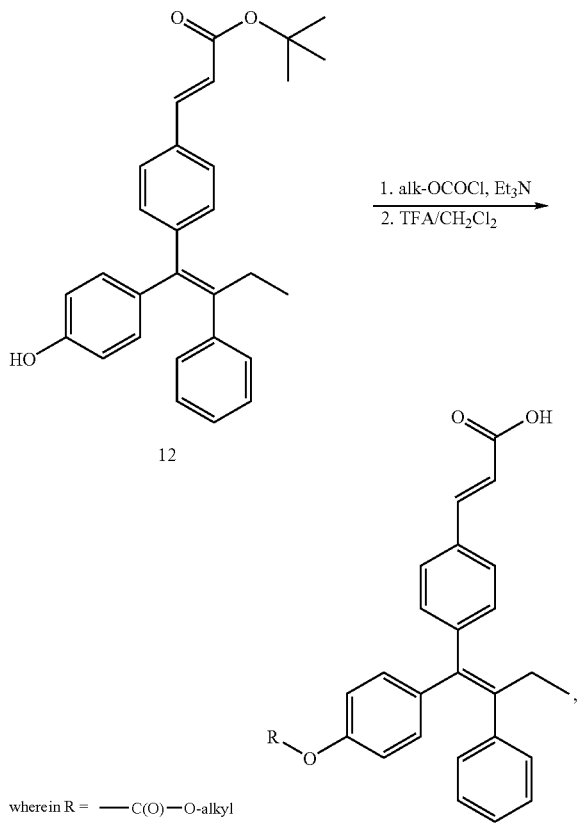

wherein R = —C(O)—O-alkyl

IX

EXAMPLES

The following specific examples are included as illustrations and are not to be construed as limiting the scope of the present invention.

Example 1 (1)

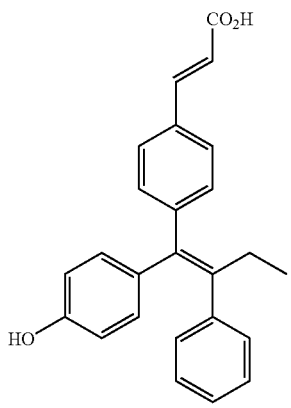

Step 1: 1-(4-Methoxyphenyl)-2-phenylbutan-1-one (2)

2-Phenylbutyryl chloride (50.0 mL, 299 mmol) was dissolved in anisole (75 mL) and cooled to 0° C. AlCl₃ (40.377 g, 303 mmol) was added portionwise and the resulting mixture allowed to warm to RT then stirred for 2 h. Ice was added portionwise followed by H₂O (100 mL). The mixture was extracted with CH₂Cl₂ (3×100 mL) and the combined organics dried (MgSO₄) and concentrated. The residue was distilled to remove the remaining anisole (1 mm Hg, 40-55° C.) to provide 2 (77.27 g, 100%) as a tan oil. ¹H NMR (400 MHz, CDCl₃): δ 0.90 (t, J=7.5 Hz, 3H), 1.85 (dq, 1H), 2.18 (dq, 1H), 3.81 (s, 3H), 4.40 (t, J=7.2 Hz, 1H), 6.85 (d, J=5.0 Hz, 2H), 7.19 (m, 1H), 7.28 (m, 4H), 7.95 (d, J=5.0 Hz, 2H).

Step 2: 1-[4-(diethoxymethyl)phenyl]-1-(4-methoxyphenyl)-2-phenylbutan-1-ol (3)

Magnesium turnings (9.64 g, 397 mmol) were heated to 160° C. under vacuum for 2 hours, then were cooled to RT under nitrogen. THF (400 mL) was added followed by portionwise addition of 4-bromobenzaldehyde diethyl acetal (80.0 mL, 393 mmol). The mixture was heated with a heat gun to initiate the reaction, then allowed to stir at RT (while gently refluxing) for 90 min. The resulting dark red solution was cooled to 0° C. and a solution of 2 (77.27 g, 304 mmol) in THF (50 mL) was added. The mixture was stirred at RT for 3 hours. Saturated aqueous NH₄Cl (150 mL) and H₂O (150 mL) were added and the two layers were separated. The aqueous layer was extracted with Et₂O (3×100 mL), and the combined organics were dried (MgSO₄) and concentrated to provide 3 as a light yellow oil that was carried on without further purification. ¹H NMR (400 MHz, CDCl₃): δ 0.72 (t, J=7.3 Hz, 3H), 1.25 (t, J=7.0 Hz, 6H), 1.77 (q, J=7.3 Hz, 2H), 2.35 (s, 1H), 3.69 (s, 3H), 3.52-3.65 (m, 5H), 5.50 (s, 1H), 6.62 (d, J=8.8 Hz, 2H), 7.08 (m, 1H), 7.12 (m, 6H), 7.44 (d, J=8.2 Hz, 2H), 7.53 (d, J=8.2 Hz, 2H).

Step 3: 4-[1-(4-methoxyphenyl)-2-phenylbut-1-enyl]benzaldehyde (4)

A solution of compound 3 (163.09 g, 375 mmol) in EtOH (750 mL) was charged with concentrated aqueous HCl (150 mL) and the resulting solution heated at 80° C. for 90 min. The solution was allowed to cool to RT and then was concentrated to the aqueous layer. H₂O (500 mL) was added and the mixture extracted with CH₂Cl₂ (3×150 mL). The combined organic layers were dried (MgSO₄) and concentrated to provide 4 (119.78 g, 93% over 2 steps) as a brown oil (3:1 mixture of Z:E isomers). The mixture was carried on without further purification. Z-isomer: ¹H NMR (400 MHz, CDCl₃): δ 0.94 (t, J=7.5 Hz, 3H), 2.45 (q, J=7.5 Hz, 2H), 3.68 (s, 3H), 6.56 (d, J=8.6 Hz, 2H), 6.75 (d, J=8.6 Hz, 2H), 7.08-7.21 (m, 5H), 7.41 (d, J=8.1 Hz, 2H), 7.87 (d, J=8.1 Hz, 2H), 10.02 (s, 1H). E-isomer: ¹H NMR (CDCl₃): δ 0.97 (t, J=7.4 Hz, 3H), 2.52 (q, 7.4 Hz, 2H), 3.83 (s, 3H), 6.90 (d, J=8.3 Hz, 2H), 7.03 (d, J=8.3 Hz, 2H), 7.0-8-7.21 (m, 7H), 7.51 (d, J=8.1 Hz, 2H), 9.83 (s, 1H).

Step 4: Ethyl (2E)-3-{4-[(1Z)-1-(4-methoxyphenyl)-2-phenylbuten-1-enyl]phenyl}prop-2-enoate (5)

Compound 4 was dissolved in CH₃CN (700 mL) and triethyl phosphonoacetate (88.5 mL, 446 mmol) added followed by LiCl (29.794 g, 703 mmol) and DBU (60.0 mL, 401 mmol). The mixture was allowed to stir at RT for 90 minutes then concentrated. H₂O (500 mL) was added and the mixture extracted with CH₂Cl₂ (3×150 mL). The combined organics were dried (MgSO₄) and concentrated. The residue was recrystallized from hexanes to provide 5 (39.80 g, 32%) as pale yellow needles in a 98:2 ratio of Z:E isomers. ¹H NMR (400 MHz, CDCl₃): δ 0.94 (t, J=7.4 Hz, 3H), 1.35 (t, J=7.2

Hz, 3H), 2.47 (q, J=7.4 Hz, 2H), 3.68 (s, 3H), 4.27 (q, J=7.2 Hz, 2H), 6.43 (d, J=16.0 Hz, 1H), 6.55 (d, J=8.8 Hz, 2H), 6.76 (d, J=8.8 Hz, 2H), 7.11-7.20 (m, 5H), 7.26 (d, J=8.3 Hz, 2H), 7.51 (d, J=8.3 Hz, 2H), 7.70 (d, J=16.0 Hz, 1H).

Step 5: (2E)-3-{4-[(1Z)-1-(4-Methoxyphenyl)-2-phenylbut-1-enyl]phenyl}prop-2-enoic acid (6)

Compound 5 (39.80 g, 96.5 mmol) was dissolved in EtOH (300 mL) and THF (300 mL). 1 M aqueous NaOH (250 mL, 250 mmol) was added and the solution refluxed for 2 h. The reaction was cooled to RT and then acidified to pH 2 with 6N aq. HCl. H$_2$O (750 mL) and CH$_2$Cl$_2$ (500 mL) were added and the two layers were separated. The aqueous layer was extracted with CH$_2$Cl$_2$ (2×100 mL). The combined organics were dried (Na$_2$SO$_4$) and concentrated to provide the title compound, 6 (39.34 g, 100%), as a pale yellow solid. $^1$H NMR (400 MHz, DMSO-d$_6$): δ 0.95 (t, J=7.4 Hz, 3H), 2.48 (q, J=7.4 Hz, 2H), 3.69 (s, 3H), 6.46 (d, J=15.8 Hz, 1H), 6.56 (d, J=8.6 Hz, 2H), 6.77 (d, J=8.6 Hz, 2H), 7.10-7.12 (m, 3H), 7.13-7.19 (m, 2H), 7.28 (d, J=8.3 Hz, 2H), 7.54 (d, J=8.3 Hz, 2H), 7.80 (d, J=15.8 Hz, 1H).

Step 6: (2E)-3-{4-[(1Z)-1-(4-Hydroxyphenyl)-2-phenylbut-1-enyl]phenyl}prop-2-enoic acid (1, Compound 1)

Compound 6 (10.30 g, 26.8 mmol) was dissolved in CH$_2$Cl$_2$ (250 mL) and cooled to 0° C. under N$_2$. BBr$_3$ (7.50 mL, 79.3 mmol) was added dropwise and the resulting solution was allowed to stir at 0° C. for 2 h. i-ProH (50 mL) was carefully added. The mixture was allowed to stand at RT for 30 min during which time a precipitate formed. The mixture was filtered to provide the title compound 1 (3.88 g, 39%), as a pale yellow solid; mp 263-265° C.; $^1$H NMR (DMSO-d$_6$): δ 0.83 (t, J=7.6 Hz, 3H), 2.35 (q, J=7.5 Hz, 2H), 6.39 (d, J=8.6 Hz, 2H), 6.49 (d, J=16.1 Hz, 1H), 6.59 (d, J=8.6 Hz, 2H), 7.08-7.10 (m, 3H), 7.15-7.21 (m, 4H), 7.57 (d, J=16.1 Hz, 1H), 7.65 (d, J=8.1 Hz, 2H), 9.12 (s, 1H), 12.36 (br s, 1H); MS m/z 371 (M+H)$^+$; Anal. calculated for C$_{25}$H$_{22}$NO$_3$.0.62H$_2$O: C, 78.68; H, 6.14; Found: C, 78.68; H, 6.02.

Example 2 (7, Preparation of Ester Prodrugs—Method A)

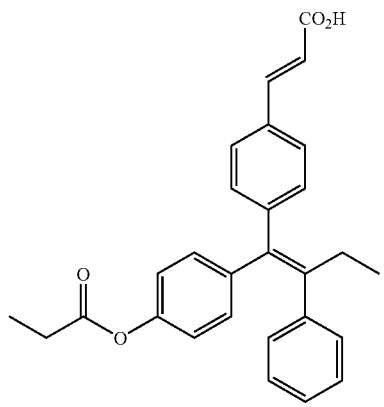

Step 1: 1-(4-hydroxyphenyl)-2-phenylbutan-1-one (8)

A 5.0 L round bottom flask was charged with 164.2 (1.00 mol) (±)-2-phenylbutyric acid (III) and 110.3 g (1.02 mol) anisole and anhydrous toluene (575 mL) and stirred until dissolved. The resulting solution was cooled to 10° C. and 367.5 g (1.75 mol) TFAA added such that the temperature did not rise above 15° C. The solution was heated to 35° C. for 1 h then at 40° C. for 72 h. The solution was cooled to 20° C. and toluene (1300 mL) added followed by 2N NaOH (1.80 mol) with external cooling and vigorous stirring at a rate such that the reaction temperature did not rise above 35° C. The mixture was stirred for 1 h and the pH then adjusted to 10 by addition of 2N NaOH. The aqueous layer was removed and the upper organic layer was washed with H$_2$O (900 mL). The aqueous layer was removed and the toluene layer concentrated to ~1000 mL via atmospheric distillation. This solution was then quickly added to a stirred mixture of 266.7 g AlCl$_3$ (2.00 mol) and anhydrous toluene (900 mL) at 70° C. The solution was stirred at 70° C. for 1 h, cooled to 15° C., and then added to water (1000 mL, 15° C.) with cooling such that the temperature did not exceed 40° C. After complete addition and cooling to 25° C., EtOAc (900 mL) was added and then stirred for 5 minutes. The lower aqueous layer was removed and the organic layer washed with water (1000 mL). The organic layer was concentrated under reduced pressure (~60° C.) to ~1000 mL. The solution was then cooled to 50° C. and hexanes (660 mL) added while maintaining an internal temperature of >50° C. The solution was then cooled slowly to 10° C. during which time crystallization occurred. The mixture was stirred for an additional 30 minutes and filtered through a medium glass fritted funnel and the filter cake washed with cold hexanes (330 mL). The material was dried to constant weight in a vacuum oven at 40° C. to yield 183.1 g (76%) of 8 as a cream solid; mp 127-129° C.; $^1$HNMR (400 MHz, DMSO-d$_6$): δ 0.80 (t, J=7.3 Hz, 3H), 1.69 (h, J=7.2 Hz, 1H), 2.04 (h, J=7.2 Hz, 1H), 4.62 (t, J=7.2 Hz, 1H), 6.79 (d, J=8.7 Hz, 2H), 7.15-7.33 (m, 5H), 7.91 (d, J=8.7 Hz, 2H), 10.32 (s, 1H).

Step 2: 2-phenyl-1-[4-(tetrahydro-2H-pyran-2-yloxy) phenyl] butan-1-one (9)

A mixture of compound 8 (908 g, 3.78 mol) in 1,2-dichloroethane (6.36 L) stirred at 30° C. was treated with dihydropyran (1590 g, 18.9 mol) in a single portion. The resulting solution was treated with CaCl$_2$ (83.8 g, 0.76 mmol) in a single portion and the reaction warmed at 70° C. for 16 h. The reaction was filtered through celite and the solid washed with 1,2-dichloroethane (2×900 mL). The filtrate was concentrated by distillation to approximately 5 L and heptane added (9 L). The reaction solution was again concentrated by distillation to approximately 7 L and then cooled slowly and held at 5° C. for 1 h. The solids were filtered, washed with heptane (2×1.8 L) and dried in vacuo at 40° C. to afford 1134 g (93%) of 9 as a solid. $^1$HNMR (400 MHz, DMSO-d$_6$): δ 0.79 (t, J=7.3 Hz, 3H), 1.49-1.83 (m, 8H), 2.03 (h, J=7.0 Hz, 1H), 3.49-3.66 (m, 2H), 4.65 (t, J=7.2 Hz, 1H), 7.02 (d, J=8.4 Hz, 2H), 7.13-7.30 (m, 5H), 7.97 (d, J=8.4 Hz, 2H).

Step 3: 4-[(1Z)-1-(4-hydroxyphenyl)-2-phenylbut-1-enyl]benzaldehyde (10)

A three-neck flask equipped with mechanical stirrer, thermometer, and nitrogen inlet was charged with 4-bromobenzaldehydediethyl acetal (800 g, 2.47 mol) and THF (7.2 L).

The contents were cooled to −65° C. and treated with a 2.5M solution of n-BuLi in hexanes (1.23, 3.08 mol) at a rate to maintain temperature <−65° C. The solution was then treated with a solution of 9 (800 g, 2.47 mol) in THF (2.4 L) at a rate to maintain temperature <−65° C. The resulting solution was allowed to warm to ambient temperature over a 1 h period. At 20° C. the reaction was quenched by addition of a saturated aqueous NH$_4$Cl solution (4 L) followed by EtOAc (4 L). After mixing well, the lower aqueous layer was separated and the organic layer washed with H$_2$O (2×4 L). The organic layer was evaporated under reduced pressure to approximately 4 L. tert-BuOH (8 L) was added and evaporation continued to a volume of approximately 4 L. The solution was heated to 65° C. and treated with 3 N aqueous HCl (80 mL) and maintained at 65° C. for approximately 1 h. The reaction solution was diluted with heptane (8 L) and then cooled slowly to 5° C. and maintained for 1 h. The solids were collected by filtration, washed with heptane (2×1.5 L), and dried in vacuo at 40° C. to afford 511 g of 10 (63%) as a 98:2 mixture of Z:E isomers. $^1$HNMR (400 MHz, DMSO-d$_6$): δ 0.83 (t, J=7.3 Hz, 3H), 2.33 (q, J=7.3 Hz, 2H), 6.41 (d, J=8.4 Hz, 2H), 6.60 (d, J=8.4 Hz, 2H), 7.10-7.20 (m, 5H), 7.40 (d, J=8.1 Hz, 2H), 7.90 (d, J=8.0 Hz, 2H), 9.25 (s, 1H), 9.98 (s, 1H).

Step 4: 4-[(1Z)-1-(4-formylphenyl)-2-phenylbut-1-enyl]phenyl propionate (11)

To a stirred mixture of 10 (28.9 g, 85.2 mmol) in EtOAc (200 mL) under a nitrogen atmosphere was added Et$_3$N (9.49 g, 94.0 mmol) at 25° C. The resulting solution was treated with a solution of propionic anhydride (12.2 g, 93.8 mmol) in EtOAc (25 mL) over a 5 minute period. The resulting mixture was allowed to stir at 60° C. for 5 h. The rapidly stirred mixture was quenched by addition of H$_2$O (125 mL) and then the lower aqueous phase removed. The organic phase was washed with H$_2$O (2×125 mL) and then evaporated under reduced pressure to 100 mL. Heptane (330 mL) was added and the reaction distilled to approximately 200 mL at a reflux temperature of 90° C. The reaction was cooled to ~50° C. and diluted with MTBE (25 mL) and then cooled slowly to 10-15° C. and held for 1 h. The product was filtered, washed with heptane (2×50 mL) then dried under vacuum at 40° C. to yield 29.48 g (90%) of 11 as a white solid. $^1$HNMR (400 MHz, DMSO-d$_6$): δ 0.85 (t, J=7.3 Hz, 3H), 2.35 (q, J=7.3 Hz, 2H), 6.79 (d, J=8.6 Hz, 2H), 6.85 (d, J=8.6 Hz, 2H), 7.11-7.21 (m, 5H), 7.45 (d, J=8.0 Hz, 2H), 7.92 (d, J=8.0 Hz, 2H), 9.99 (s, 1H).

Step 5: (2E)-3-(4-{(1Z)-2-phenyl-1-[4-(propionyloxy)phenyl]but-1-enyl}phenyl)prop-2-enoic acid (7)

To a mixture of 11 (20.0 g, 52 mmol) and malonic acid (8.10 g, 100 mmol) was added, sequentially, CH$_3$CN (100 mL), pyridine (2.1 mL, 30 mmol) and morpholine (0.09 mL, 1.0 mmol). The mixture was then heated to reflux and the solvent distilled. The volume of the reaction was maintained constant by addition of fresh CH$_3$CN until ~30 volumes of solvent were distilled. The reaction was then cooled to 5° C. and a solution of acetic acid (2.08 mL, 36 mmol) in CH$_3$CN (20 mL) added. The precipitated solid was filtered, washed with cold CH$_3$CN (40 mmol) and H$_2$O (40 mL) then slurried overnight in heptane (150 mL) at 35° C. The solid was filtered, rinsed with heptane (40 mL) and dried overnight in vacuo to yield 17.8 g (80%) of the title compound 7 as a white solid. $^1$HNMR (DMSO-d$_6$): δ 0.26 (s, 6H), 0.83 (t, J=7.5 Hz, 3H), 0.94 (s, 9H), 2.35 (q, J=7.5 Hz, 2H), 6.39 (d, J=8.4 Hz, 2H), 6.53 (d, J=16 Hz, 1H), 6.58 (d, J=8.4 Hz, 2H), 7.06-7.18 (m, 5H), 7.2 (d, J=8 Hz, 2H), 7.59 (d, J=16 Hz, 1H), 7.69 (d, J=8 Hz, 2H), 9.19 (s, 1H); MS, m/z 485 (M+H)$^+$.

Example 3 (7, Preparation of Ester Prodrugs—Method B)

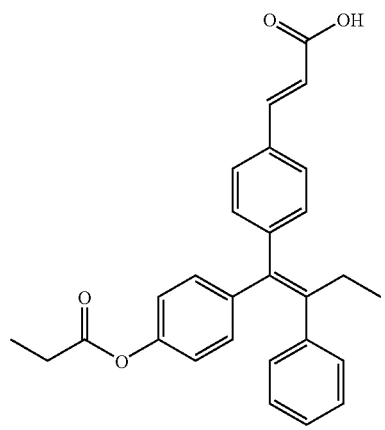

(2E)-3-(4-{(1Z)-2-phenyl-1-[4-(propionyloxy)phenyl]but-1-enyl}phenyl)prop-2-enoic acid (7)

To a stirred solution of the phenol 1 (1.0 g, 2.7 mmol) and Et$_3$N (1.0 mL, 7.3 mmol) in THF (20 mL) at 5° C. was added, over 30 min, a solution of propionyl chloride (0.59 mL, 6.7 mmol) in THF (10 mL). After stirring at 5° C. for 1 h, H$_2$O (30 mL) was added and stirring continued for an additional 1 h. The reaction was diluted with Et$_2$O (60 mL), the layers separated, and the organics washed with H$_2$O (2×40 mL) and concentrated to an oil. The oil was taken up in fresh THF (60 mL) followed by H$_2$O (20 mL) and saturated NaHCO$_3$ (20 mL) and stirred at ambient temperature for 8 h. The reaction was diluted with Et$_2$O (20 mL) followed by H$_2$O (30 mL) and the layers separated. The aqueous fraction was extracted with Et$_2$O (2×30 mL) and the combined organics were washed with brine (50 mL), dried (MgSO$_4$) and concentrated to a solid. This solid was stirred, as a suspension, in 20% (v/v) Et$_2$O in hexane (15 mL) for 2 h. The resulting solid was filtered, rinsed with hexane and dried to afford the title compound, 7, as a pale yellow solid (738 mg, 64%); mp 158-160° C.; $^1$HNMR (400 MHz, DMSO-d$_6$): δ 0.85 (t, 3H), 1.04 (t, 3H), 2.39 (q, 2H), 2.47 (q, 2H), 6.50 (d, J=15.9 Hz, 1H), 6.78 (d, J=8.6 Hz, 2H), 6.84 (d, J=8.6 Hz, 2H), 7.09-7.19 (m, 5H), 7.24 (d, J=8.1 Hz, 2H), 7.55 (d, J=15.9 Hz, 1H), 7.68 (d, J=7.9 Hz, 2H), 12.35 (br, 1H); MS m/z, 449 (M+Na)$^+$, 425 (M−H)$^{--}$; Anal. calculated for C$_{28}$H$_{26}$O$_4$: C, 78.85; H, 6.15; Found: C, 78.89; H, 6.22.

Example 4 (12)

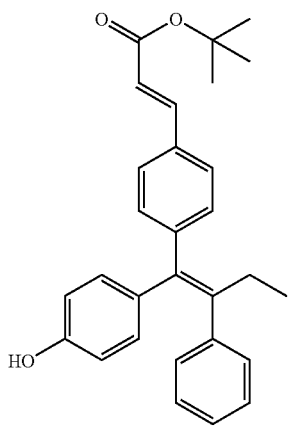

Step 1: 1-Bromo-4-(methoxymethoxy)benzene (13)

To a suspension of 60% NaH in mineral oil (12.7 g, 31.8 mmol) in anhydrous THF (300 mL) at 0° C. was added 4-bromophenol (50.0 g, 28.9 mmol) dissolved in THF (100 mL) dropwise over 1 h. The reaction mixture was stirred at 0° C. for 30 min, and chloromethylmethyl ether (24.8 mL, 32.6 mmol) dissolved in THF (30 mL) was added dropwise over 20 min. The reaction mixture was stirred overnight at RT. $H_2O$ (250 mL) was added, and the mixture was extracted with $Et_2O$ (2×250 mL). The combined ethereal extracts were washed with brine (500 mL), dried over $MgSO_4$, and concentrated. The residue was distilled under vacuum to afford 57.6 g (92%) of 13 as a colorless oil. $^1H$ NMR (400 MHz, DMSO-$d_6$): δ 3.33 (s, 3H), 5.15 (s, 2H), 6.96 (d, J=9.0 Hz, 2H), 7.43 (d, J=9.0 Hz, 2H).

Step 2: N-Methoxy-N-methyl-2-phenylbutanamide (14)

To a stirred solution of pyridine (33.1 mL, 40.9 mmol) and N,O-dimethylhydroxylamine hydrochloride (26.0 g, 26.7 mmol) in anhydrous $CH_2Cl_2$ (300 mL) at 0° C. was added dropwise 2-phenylbutyryl chloride (37.4 g, 20.5 mmol) dissolved in THF (100 mL). The reaction mixture was stirred overnight at RT. $H_2O$ (300 mL) was added, and the mixture was extracted with $CH_2Cl_2$ (2×200 mL). The combined extracts were washed successively with 5% aqueous HCl (300 mL), 5% aqueous $NaHCO_3$ (300 mL), $H_2O$ (300 mL), and brine (300 mL). The mixture was dried over $Na_2SO_4$, filtered, and concentrated to afford 41.6 g (98%) of 14 as a colorless oil which was used without further purification. $^1$HNMR (400 MHz, $CDCl_3$): δ 0.87 (t, J=7.3 Hz, 3H), 1.74 (h, J=7.1 Hz, 1H), 2.08 (h, J=7.1 Hz, 1H), 3.14 (s, 3H), 3.46 (s, 3H), 3.88 (br s, 1H), 7.19-7.33 (m, 5H).

Step 3: 1-[4-(Methoxymethoxy)phenyl]-2-phenylbutan-1-one (15)

To a stirred solution of 13 (99.0 g, 0.46 mol) in anhydrous THF (750 mL) was added n-BuLi (1.6 M in hexanes, 310 mL, 0.50 mol) dropwise at −78° C. The reaction mixture was stirred for 30 min and 14 (90.1 g, 0.43 mol) dissolved in THF (500 mL) was added dropwise. The reaction mixture was stirred at −78° C. for 1 h and then slowly warmed to 0° C. $H_2O$ (500 mL) was added and the volatiles were removed under reduced pressure. The residue was extracted with $Et_2O$ (3×500 mL) and the combined extracts were washed with water (500 mL) and brine (500 mL). The mixture was dried over $MgSO_4$ and concentrated. The residue was recrystallized from hexanes to afford 97.6 g (80%) of 15 as white needles. $^1$HNMR (400 MHz, DMSO-$d_6$): δ 0.79 (t, J=7.3 Hz, 3H), 1.68 (h, J=7.0 Hz, 1H), 2.03 (h, J=7.0 Hz, 1H), 3.32 (s, 3H), 4.65 (t, J=7.3 Hz, 1H), 5.21 (s, 2H), 7.03 (d, J=8.8 Hz, 2H), 7.15 (t, J=7.1 Hz, 1H), 7.23-7.30 (m, 4H), 7.98 (d, J=8.8 Hz, 2H).

Step 4: 1-[4-(Diethoxymethyl)phenyl]-1-[4-(methoxymethoxy)phenyl]-2-phenylbutan-1-ol (16)

To a stirred solution of 4-bromobenzaldehyde diethyl acetal (107 g, 0.41 mol) in anhydrous THF (750 mL) was added n-BuLi (1.6 M in hexanes, 268 mL, 0.43 mol) dropwise at −78° C. After stirring for 1 h at −78° C., a solution of 15 (97.6 g, 0.34 mol) in THF (750 mL) was cannulated into the reaction mixture portionwise. The mixture was stirred overnight at RT, $H_2O$ (500 mL) was added, and the volatiles were removed under reduced pressure. The residue was extracted with $Et_2O$ (3×500 mL) and the combined extracts washed with $H_2O$ (500 mL) and brine (500 mL). The mixture was dried over $MgSO_4$ and concentrated to afford 194 g of 16 that was used without further purification. $^1$HNMR (400 MHz, DMSO-$d_6$): δ 0.58 (t, J=7.3 Hz, 3H), 1.12 (m, 6H), 1.52 (m, 1H), 1.70 (m, 1H), 3.23 (s, 3H), 3.40-3.65 (m, 5H), 4.98 (s, 2H), 5.41 (s, 1H), 5.51 (s, 1H), 6.62 (d, J=8.8 Hz, 2H), 6.96-7.06 (m, 3H), 7.17-7.23 (m, 4H), 7.31 (d, J=8.0 Hz, 2H), 7.61 (d, J=8.4 Hz, 2H).

Step 5: 4-[(1Z)-1-(4-Hydroxyphenyl)-2-phenylbut-1-enyl]benzaldehyde (10)

To a solution of 16 (194 g, 0.42 mol) in EtOH (1.25 L) was added 12 M HCl (250 mL). The reaction mixture was refluxed for 3 h, cooled to RT, and the volatiles were removed under reduced pressure. $H_2O$ (750 mL) was added and the mixture was extracted with ether (3×500 mL). The combined ethereal extracts were washed with $H_2O$ (750 mL), brine (750 mL), and dried over $MgSO_4$. Concentration followed by recrystallization from hexanes afforded 52.8 g (38%) of 10 as a white solid. $^1$HNMR (400 MHz, DMSO-$d_6$): δ 0.83 (t, J=7.3 Hz, 3H), 2.33 (q, J=7.3 Hz, 2H), 6.40 (d, J=8.4 Hz, 2H), 6.60 (d, J=8.4 Hz, 2H), 7.10-7.20 (m, 5H), 7.40 (d, J=7.9 Hz, 2H), 7.90 (d, J=8.1 Hz, 2H), 9.23 (s, 1H), 9.98 (s, 1H).

Step 6: tert-Butyl (2E)-3-{4-[(1Z)-1-(4-hydroxyphenyl)-2-phenylbut-1-enyl]phenyl}prop-2-enoate (12)

To a stirred solution of (tert-butoxycarbonylmethylene)triphenylphosphorane (5.19 g, 13.8 mmol) in $CH_2Cl_2$ (200 mL) was added 10 (2.29 g, 7.0 mmol) dissolved in $CH_2Cl_2$ (100 mL) dropwise at 0° C. The reaction mixture was stirred at RT for 2 h. Silica gel (12.0 g) was added, and the volatiles were removed under reduced pressure. Flash chromatography (20:1 to 4:1 hexane:EtOAc), followed by recrystallization (hexane/EtOAc) afforded 2.0 g (67%) of 12 as a white solid. $^1$HNMR (400 MHz, DMSO-$d_6$): δ 0.83 (t, J=7.3 Hz, 3H), 1.46 (s, 9H), 2.35 (q, J=7.3 Hz, 2H), 6.39 (d, J=8.4 Hz, 2H), 6.48 (d, J=16.0 Hz, 1H), 6.59 (d, J=8.4 Hz, 2H), 7.07-7.20 (m, 7H), 7.53 (d, J=16.0 Hz, 1H), 7.66 (d, J=8.1 Hz, 2H), 9.19 (s, 1H); MS, m/z, 425 (M−H).

This material was contaminated with up to 25% of the undesired E-isomer, tert-Butyl (2E)-3-{4-[(1E)-1-(4-hydroxyphenyl)-2-phenylbut-1-enyl]phenyl}prop-2-enoate (17). ¹HNMR (400 MHz, DMSO-d₆): δ 0.83 (t, J=7.5 Hz, 3H), 1.42 (s, 9H), 2.40 (q, J=7.5 Hz, 2H), 6.32 (d, J=15.9 Hz, 1H), 6.74 (d, J=8.4 Hz, 2H), 6.80 (d, J=8.4 Hz, 2H), 6.98 (d, J=7.4 Hz, 2H), 7.06-7.17 (m, 5H), 7.31 (d, J=8.4 Hz, 2H), 7.34 (d, J=16 Hz, 1H), 9.44 (s, 1H). The pure (>95% by HPLC) 12 (Z-isomer) was prepared by recrystallization from EtOAc or by separation by RP-HPLC using a C18 Luna column (150× 21.2 mm, 5 p particle size) with 77:33 CH₃CN/H₂O (0.1% TFA) for 20 min at a flow rate of 20 mL/min (Tr=15.08 min).

Representative procedure for preparation of prodrugs of 1 from t-butyl ester 12 and acid chlorides (Method C):

Example 5 (18)

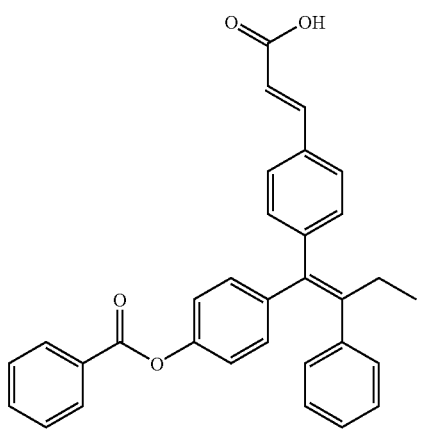

Step 1: 4-((1Z)-1-{4-[(1E)-3-tert-butoxy-3-oxoprop-1-enyl]phenyl}-2-phenylbut-1-enyl)phenyl benzoate (19)

To a solution of 12 (100 mg, 0.23 mmol) in CH₂Cl₂ (5 mL) was added Et₃N (0.13 mL, 0.94 mmol) followed by the addition of benzoyl chloride (35 mg, 0.24 mmol). The reaction mixture was stirred at RT for 2 hr. The solution was washed with H₂O (5 mL) and the organic layer dried (Na₂SO₄), and concentrated to provide a tan solid. This solid was then purified by chromatography (silica, 1:4 ethyl acetate/hexanes) to provide 19 as a white solid (80 mg, 67%). ¹HNMR (400 MHz, DMSO-d₆): δ 0.86 (t, 3H), 1.47 (s, 9H), 2.40 (q, 2H), 6.50 (d, J=16 Hz, 1H), 6.89 (d, J=8 Hz, 2H), 6.95 (d, J=8 Hz, 2H), 7.12-7.16 (m, 3H), 7.17-7.22 (m, 4H), 7.53 (d, J=8 Hz, 2H), 7.56 (d, J=16 Hz, 1H), 7.62-7.72 (m, 3H), 8.01 (d, J=8 Hz, 2H).

Step 2: (2E)-3-(4-{(1Z)-1-[4-(benzoyloxy)phenyl]-2-phenylbut-1-enyl}phenyl)prop-2-enoic acid (18)

Compound 19 was dissolved in CH₂Cl₂ (10 mL) and cooled to 0° C. in an ice bath. TFA (5 mL, 65 mmol) was and the mixture stirred in an ice bath for 2 h. The reaction was concentrated at RT and dried under high vacuum to provide the title compound, 18, as a white solid (53 mg, 74%). ¹HNMR (400 MHz, DMSO-d₆): δ 0.86 (t, 3H), 2.40 (q, 2H), 6.51 (d, J=16 Hz, 1H), 6.90 (d, J=8 Hz, 2H), 6.96 (d, J=8 Hz, 2H), 7.14-7.18 (m, 3H), 7.16-7.20 (m, 4H), 7.54 (d, J=8 Hz, 2H), 7.56 (d, J=16 Hz, 1H), 7.66-7.71 (m, 3H), 8.03 (d, J=8 Hz, 2H), 12.2 (br s, 1H); MS, m/z, 473 (M−H)⁻.

The following ester prodrugs were prepared using a similar procedure as described for the benzoate ester 18:

Example 6 (20)

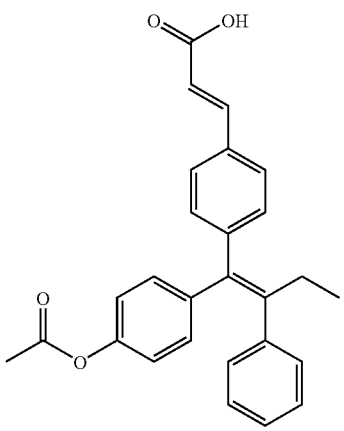

(2E)-3-(4-{(1Z)-1-[4-(acetyloxy)phenyl]-2-phenyl-but-1-enyl}phenyl)prop-2-enoic acid (20)

Prepared from 12 and acetyl chloride. ¹HNMR (400 MHz, DMSO-d₆): δ 0.84 (t, 3H), 2.15 (s, 3H), 2.37 (q, 2H), 6.50 (d, J=16 Hz, 1H), 6.76 (d, J=8 Hz, 2H), 6.84 (d, J=8 Hz, 2H), 7.09-7.19 (m, 5H), 7.24 (d, J=8 Hz, 2H), 7.57 (d, J=16 Hz, 1H), 7.68 (d, J=8 Hz, 2H), 12.3 (br s, 1H); MS, m/z, 411 (M−H)⁻.

Example 7 (7)

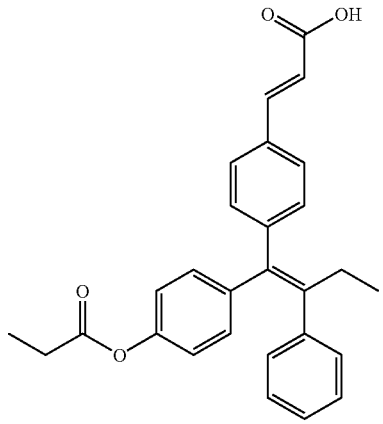

(2E)-3-(4-{(1Z)-2-phenyl-1-[4-(propionyloxy)phenyl]but-1-enyl}phenyl)prop-2-enoic acid (7)

Prepared from 12 and propanoyl chloride. ¹HNMR (400 MHz, DMSO-d₆): δ 0.84 (t, 3H), 1.05 (t, 3H), 2.37 (q, 2H), 2.42 (q, 2H), 6.51 (d, J=16 Hz, 1H), 6.78 (d, J=8 Hz, 2H), 6.84 (d, J=8 Hz, 2H), 7.10-7.18 (m, 5H), 7.25 (d, J=8 Hz, 2H), 7.57 (d, J=16 Hz, 1H), 7.69 (d, J=8 Hz, 2H), 12.3 (br s, 1H); MS, m/z, 425 (M−H)⁻.

Example 8 (21)

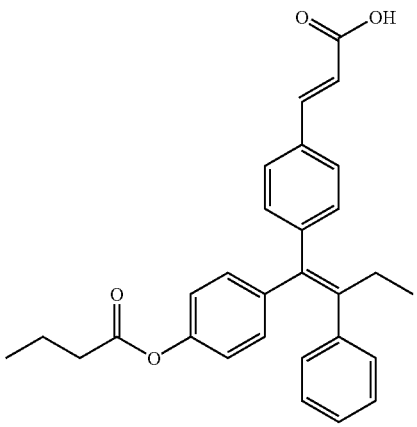

(2E)-3-(4-{(1Z)-1-[4-(butyryloxy)phenyl]-2-phenyl-but-1-enyl}phenyl)prop-2-enoic acid (21)

Prepared from 12 and butanoyl chloride. ¹HNMR (400 MHz, DMSO-d$_6$): δ 0.84 (t, 3H), 0.94 (t, 3H), 1.58 (m, 2H), 2.37 (q, 2H), 2.46 (q, 2H), 6.52 (d, J=16 Hz, 1H), 6.78 (d, J=8 Hz, 2H), 6.84 (d, J=8 Hz, 2H), 7.10-7.20 (m, 5H), 7.25 (d, J=8 Hz, 2H), 7.58 (d, J=16 Hz, 1H), 7.69 (d, J=8 Hz, 2H), 12.3 (br s, 1H); MS, m/z, 439 (M−H)⁻.

Example 9 (22)

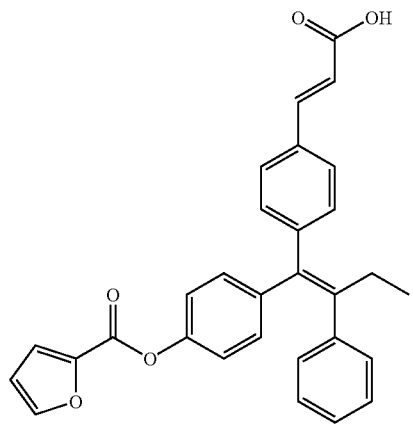

(2E)-3-(4-{(1Z)-1-[4-(2-Furoyloxy)phenyl]-2-phenyl-1-butenyl}phenyl)-2-propenoic acid (22)

Prepared from 12 and 2-furoyl chloride. Off-white solid; mp 170-172° C.; ¹HNMR (400 MHz, DMSO-d$_6$): δ 0.87 (t, J=7.2 Hz, 3H), 2.41 (q, J=7.2 Hz, 2H), 6.52 (d, J=15.8 Hz, 1H), 6.75 (dd, J=3.4, 1.5 Hz, 1H), 6.9 (d, J=8.8 Hz, 2H), 6.94 (d, J=8.8 Hz, 2H), 7.10-7.23 (m, 5H), 7.28 (d, J=8.1 Hz, 2H), 7.48 (d, J=3.4 Hz, 1H), 7.59 (d, J=15.8 Hz, 1H), 7.71 (d, J=8.1 Hz, 2H), 8.05 (br s, 1H), 12.35 (br s, 1H); MS, m/z 465 (M+1)⁺; Anal. calculated for C$_{30}$H$_{24}$O$_5$.0.50H$_2$O: C, 76.09; H, 5.32; Found: C, 76.01; H, 5.39.

Example 10 (23)

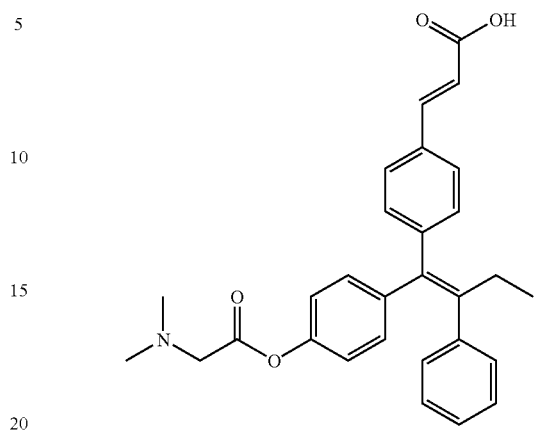

(2E)-3-[4-((1Z)-1-{4-[(N,N-dimethylglycyl)oxy]phenyl}-2-phenylbut-1-enyl)phenyl]prop-2-enoic acid (23)

Prepared from 12 and dimethylaminoacetyl chloride hydrochloride. Slightly colored solid; mp 206-208° C. (MeOH/Et$_2$O); ¹HNMR (400 MHz, DMSO-d$_6$): δ 0.87 (t, J=7 Hz, 3H), 2.41 (q, J=7 Hz, 2H), 2.85 (s, 6H), 4.37 (s, 2H), 6.52 (d, J=16 Hz, 1H), 6.92 (s, 4H), 7.08-7.20 (m, 5H), 7.26 (d, J=8.1 Hz, 2H), 7.59 (d, J=16 Hz, 1H), 7.71 (d, J=8.1 Hz, 2H), 10.02 (br s, 1H), 12.4 (br s, 1H); MS, m/z 456 (M+1)⁺; Anal. calculated for C$_{29}$H$_{29}$NO$_4$.1.0 CF$_3$CO$_2$H: C, 65.37; H, 5.31; N, 2.46; Found: C, 65.40; H, 5.34; N, 2.43.

Example 11 (24)

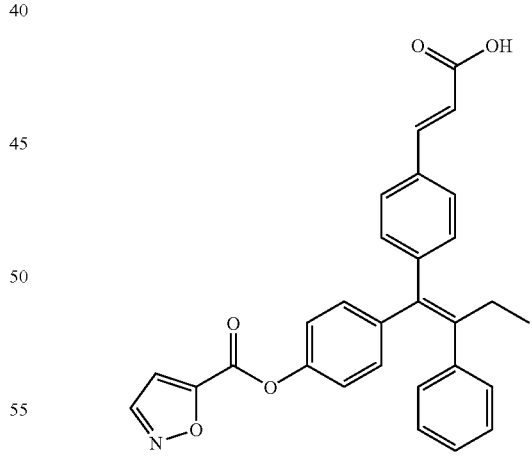

(2E)-3-[4-((1Z)-1-{4-[(5-Isoxazolylcarbonyl)oxy]phenyl}-2-phenyl-1-butenyl)phenyl]-2-propenoic acid (24)

The title compound was prepared from 12 and isoxazole-5-carbonyl chloride. Pale yellow solid; mp 141-142° C.; ¹HNMR (400 MHz, DMSO-d$_6$): δ 0.87 (t, J=7.4 Hz, 3H), 2.42 (q, J=7.4 Hz, 2H), 6.52 (d, J=16 Hz, 1H), 6.91 (d, J=8.6

Hz, 2H), 7.02 (d, J=8.6 Hz, 2H), 7.08-7.24 (m, 5H), 7.28 (d, J=8.1 Hz, 2H), 7.44 (d, J=1.9 Hz, 1H), 7.59 (d, J=16 Hz, 1H), 7.72 (d, J=8.1 Hz, 2H), 8.90 (d, J=1.9 Hz, 1H), 12.40 (s, 1H); MS, m/z 488 (M+Na)$^+$; Anal. calculated for $C_{29}H_{23}NO_2 \cdot 0.57H_2O$: C, 73.21; H, 5.11; N, 2.94; Found: C, 73.21; H, 5.28; N, 2.88.

Example 12 (25)

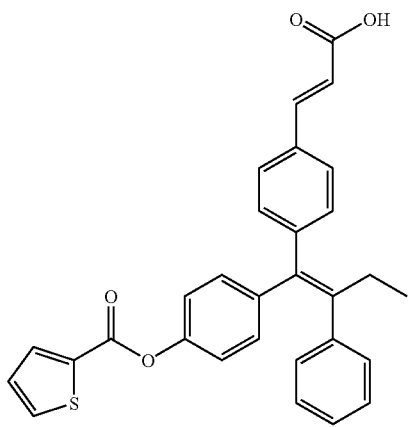

(2E)-3-[4-((1Z)-2-phenyl-1-{4-[(thien-2-ylcarbonyl)oxy]phenyl}but-1-enyl)phenyl]prop-2-enoic acid (25)

The title compound was prepared from 12 and thiophene-2-carbonyl chloride. Off-white solid; mp 175-176° C.; $^1$HNMR (400 MHz, DMSO-d$_6$): δ 0.87 (t, J=7.2 Hz, 3H), 2.42 (q, J=7.2 Hz, 2H), 6.53 (d, J=16.0 Hz, 1H), 6.90-6.97 (m, 4H), 7.15-7.29 (m, 8H), 7.60 (d, J=16 Hz, 1H), 7.72 (d, J=7.6 Hz, 2H), 7.94 (d, J=2.4 Hz, 1H), 8.04 (d, J=4.4 Hz, 1H), 12.40 (br s, 1H); MS, m/z 463 (M+H)$^+$; Anal. calculated for $C_{30}H_{24}O_4S \cdot 0.1\ CF_3CO_2H$: C, 73.73; H, 4.94; Found: C, 73.73; H, 4.78.

Example 13 (26)

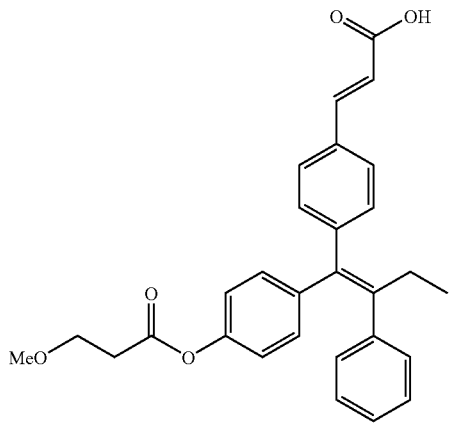

(2E)-3-[4-((1Z)-1-{4-[(methoxyacetyl)oxy]phenyl}-2-phenylbut-1-enyl)phenyl]prop-2-enoic acid (26)

The title compound was prepared from 12 and 3-methoxypropanoyl chloride. Off-white solid; mp 190-191° C.; IR (film), 2971, 2930, 1761, 1639, 1418, 1201 cm$^{-1}$, $^1$HNMR (400 MHz, CDCl$_3$): δ 0.94 (t, J=7.2 Hz, 3H), 2.48 (q, J=7.6 Hz, 2H), 2.73 (t, J=6.4 Hz, 2H), 3.36 (s, 3H), 3.71 (t, J=6.4 Hz, 2H), 6.46 (d, J=16.0 Hz, 1H), 6.76 (d, J=8.4 Hz, 2H), 6.85 (d, J=8.8 Hz, 2H), 7.08-7.17 (m, 5H), 7.25-7.29 (m, 3H), 7.54 (d, J=8.0 Hz, 2H), 7.80 (d, J=16.0 Hz, 1H), MS, m/z 480.17 (M+Na)$^+$; Anal. calculated for $C_{29}H_{28}O_5 \cdot 0.25H_2O$: C, 75.55; H, 6.23; found: C, 75.60; H, 6.12.

Example 14 (27)

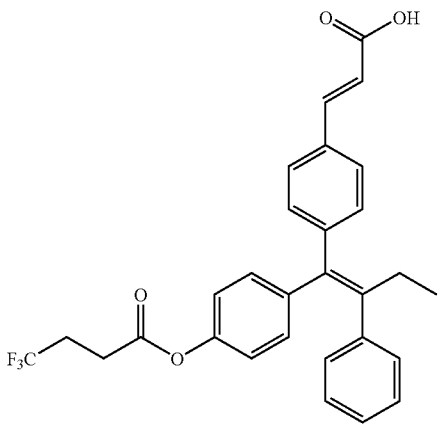

(2E)-3-[4-((1Z)-2-phenyl-1-{4-[(4,4,4-trifluorobutanoyl)oxy]phenyl}but-1-enyl)phenyl]prop-2-enoic acid (27)

The title compound was prepared from 12 and 4,4,4-trifluorobutanoyl chloride. Off-white solid; mp 162-163° C.; $^1$HNMR (400 MHz, CDCl$_3$): δ 0.96 (t, J=6.8 Hz, 3H), 2.55-2.49 (m, 4H), 2.77 (t, J=7.6 Hz, 2H), 6.47 (d, J=16 Hz, 1H), 6.75 (d, J=8.4 Hz, 2H), 6.87 (d, J=8.4 Hz, 2H), 7.09-7.19 (m, 5H), 7.26-7.30 (m, 3H), 7.55 (d, J=7.6 Hz, 2H), 7.81 (d, J=16 Hz, 1H); MS, m/z 518 (M+Na)$^+$; Anal. calculated for $C_{29}H_{25}F_3O_4 \cdot 0.35\ CF_3CO_2H$: C, 66.75; H, 4.78; Found: C, 66.77; H, 4.83.

Example 15 (28)

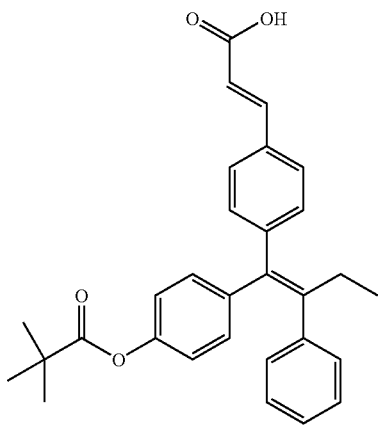

(2E)-3-[4-((1Z)-1-{4-[(2,2-dimethylpropanoyl)oxy]phenyl}-2-phenylbut-1-enyl)phenyl]prop-2-enoic acid (28)

The title compound was prepared from 12 and pivaloyl chloride. $^1$HNMR (400 MHz, DMSO-d$_6$): δ 0.85 (t, 3H), 1.19

(s, 9H), 2.38 (q, 2H), 6.50 (d, J=16 Hz, 1H), 6.75 (d, J=8 Hz, 2H), 6.84 (d, J=8 Hz, 2H), 7.19-7.09 (m, 5H), 7.23 (d, J=8 Hz, 2H), 7.56 (d, J=16 Hz, 1H), 7.68 (d, J=8 Hz, 2H), 12.3 (br s, 1H); MS, m/z, 453 (M−H)⁻.

Example 16 (29)

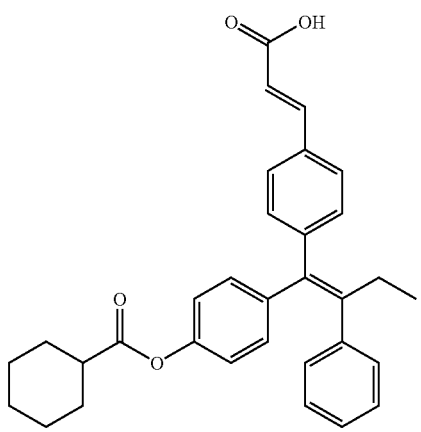

(2E)-3-[4-((1Z)-1-{4-[(cyclohexylcarbonyl)oxy]phenyl}-2-phenylbut-1-enyl)phenyl]prop-2-enoic acid (29)

The title compound was prepared from 12 and cyclohexanecarbonyl chloride. ¹HNMR (400 MHz, DMSO-d₆): δ 0.85 (t, 3H), 1.08-1.96 (m, 11H), 2.38 (q, 2H), 6.50 (d, J=16 Hz, 1H), 6.75 (d, J=8 Hz, 2H), 6.83 (d, J=8 Hz, 2H), 7.09-7.19 (m, 5H), 7.23 (d, J=8 Hz, 2H), 7.57 (d, J=16 Hz, 1H), 7.68 (d, J=8 Hz, 2H), 12.3 (br s, 1H); MS, m/z, 479 (M−H)⁻.

Preparation of ester prodrugs of 1 via Scheme 5 (Method D):

Example 17 (7)

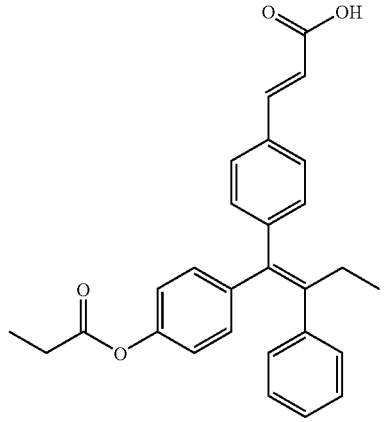

Step 1: tert-Butyl(dimethyl)silyl (2E)-3-{4-[(1Z)-1-(4-hydroxyphenyl)-2-phenyl-1-butenyl]phenyl}-2-propenoate (30)

To a suspension of compound 1 (0.57 g, 1.53 mmol) in anhydrous THF (10 mL) was added N-methylmorpholine (0.18 mL, 0.16 g, 1.64 mmol) and tert-butyldimethylsilyl chloride (0.26 g, 1.64 mmol) and the mixture was stirred at RT for 1 h. The mixture was diluted with EtOAc and washed with H₂O (2×). The organic phase was dried (Na₂SO₄), concentrated, and the residue triturated with hexanes (5 mL). The solid was filtered and washed with hexanes to provide 30 (0.52 g, 70%) as a pale yellow solid. ¹HNMR (DMSO-d₆): δ 0.26 (s, 6H), 0.83 (t, J=7.5 Hz, 3H), 0.94 (s, 9H), 2.35 (q, J=7.5 Hz, 2H), 6.39 (d, J=8.4 Hz, 2H), 6.53 (d, J=16.0 Hz, 1H), 6.58 (d, J=8.4 Hz, 2H), 7.06-7.18 (m, 5H), 7.2 (d, J=8 Hz, 2H), 7.59 (d, J=16.0 Hz, 1H), 7.69 (d, J=8 Hz, 2H), 9.19 (s, 1H); MS, m/z 485 (M+H)⁺.

Step 2: (2E)-3-(4-{(1Z)-2-Phenyl-1-[4-(propionyloxy)phenyl]-1-butenyl}phenyl)-2-propenoic acid (7)

To a solution of 30 (0.10 g, 0.20 mmol) in CH₂Cl₂ (5 mL) was added Et₃N (0.072 mL, 0.052 g, 0.51 mmol) and propionyl chloride (0.021 mL, 0.021 g, 0.22 mmol). The mixture was stirred at ambient temperature for 1 h, washed with H₂O (2×), dried (Na₂SO₄), concentrated, and dried in vacuo to give an off-white foam. This residue was dissolved in THF (3 mL) and H₂O (0.6 mL) and the mixture was stirred at ambient temperature for 5 h. Solvent was evaporated and the residue triturated with hexanes/Et₂O (5:1) to provide 7 (0.064 g, 73%) as an off-white solid, mp 155-157° C. ¹HNMR (DMSO-d₆): δ 0.86 (t, J=7.4 Hz, 3H), 1.05 (t, J=7.4 Hz, 3H), 2.4 (q, J=7.4 Hz, 2H), 2.49 (q, J=7.4 Hz, 2H), 6.51 (d, J=16 Hz, 1H), 6.79 (d, J=8.6 Hz, 2H), 6.85 (d, J=8.6 Hz, 2H), 7.10-7.22 (m, 5H), 7.25 (d, J=8.1 Hz, 2H), 7.59 (d, J=16 Hz, 1H), 7.7 (d, J=8.1 Hz, 2H), 12.33 (br s, 1H); Anal. calculated for $C_{28}H_{26}O_4 \cdot 0.25 H_2O$: C, 78.03; H, 6.20; Found: C, 78.02; H, 6.13.

The following example was similarly prepared as described for Example 17 (Scheme 5, Method D):

Example 18 (23)

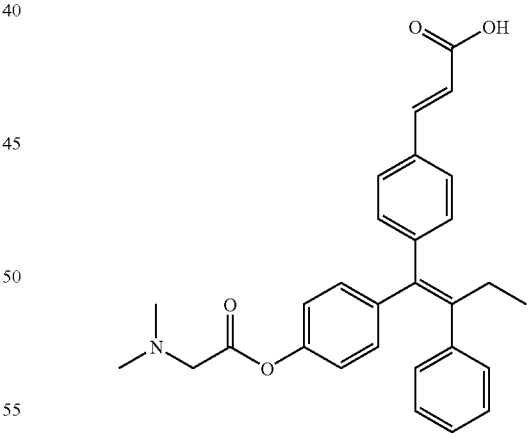

(2E)-3-[4-((1Z)-1-{4-[(N,N-dimethylglycyl)oxy]phenyl}-2-phenylbut-1-enyl)phenyl]prop-2-enoic acid (23)

Prepared from 30 and dimethylaminoacetyl chloride hydrochloride. Yellow solid foam. For ¹HNMR and MS data refer to Example 10. Anal. calculated for $C_{29}H_{29}NO_4 \cdot 1.31\ CF_3CO_2H$: C, 62.78; H, 5.05; N, 2.32; Found: C, 62.80; H, 5.25; N, 2.41.

Example 19 (31, Scheme 6)

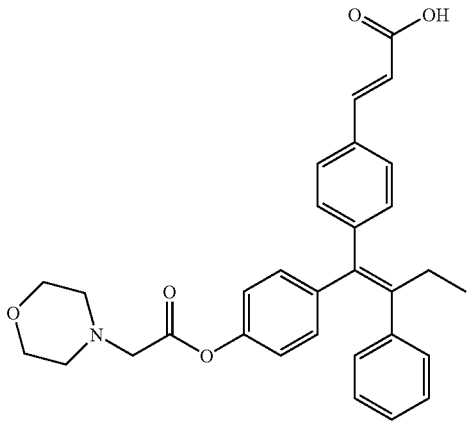

Step 1: (2E)-3-[4-((1Z)-1-{4-[(chloroacetyl)oxy]phenyl}-2-phenylbut-1-enyl)phenyl]prop-2-enoic acid (32)

To a stirred solution of 1 (780 mg, 2.1 mmol) and Et$_3$N (0.68 mL, 4.8 mmol) in THF (16 mL) at 5° C. was added a solution of chloroacetyl chloride (0.37 mL, 4.6 mmol) in THF (4 mL) over 1 h. After stirring for 1 h, H$_2$O (20 mL) was added and stirring continued at 5° C. for an additional 1.5 h. The reaction mixture was diluted with Et$_2$O (30 mL), the layers separated and the aqueous extracted with Et$_2$O (30 mL). The combined organics were washed with saturated NaHCO$_3$ (40 mL), brine (40 mL), dried (MgSO$_4$) and then concentrated to a solid. The solid was suspended in 20% Et$_2$O/hexane (20 mL) and stirred for 20 h. The resulting solid was filtered, rinsed with hexane and dried to afford 32 as a light yellow solid (718 mg, 76%). $^1$HNMR (400 MHz, DMSO-d$_6$): δ 0.85 (t, 3H), 2.39 (q, 2H), 4.57 (s, 2H), 6.51 (d, J=15.9 Hz, 1H), 6.83-6.89 (m, 4H), 7.09-7.15 (m, 5H), 7.25 (d, J=8.1 Hz, 2H), 7.58 (d, J=15.9 Hz, 1H), 7.79 (d, J=8.1 Hz, 2H), 12.39 (br, 1H).

Step 2: (2E)-3-[4-((1Z)-1-{4-[(morpholin-4-ylacetyl)oxy]phenyl}-2-phenylbut-1-enyl)phenyl]prop-2-enoic acid (31)

To a stirred solution of compound 32 (100 mg, 0.22 mmol) in THF (4 mL) was added NaI (100 mg, 0.67 mmol) and the mixture stirred for 1 h. The reaction was cooled to 5° C. and a solution of morpholine (0.029 mL, 0.33 mmol) in THF (2 mL) was added over 1 h. After stirring for 1 h, the reaction was diluted with EtOAc (40 mL) and poured into a mixture of ice water (30 mL) and 0.1 N HCl (10 mL). The layers were separated and the organic layer was washed with brine (40 mL), dried (MgSO$_4$) and concentrated. Et$_2$O (8 mL) was added and the mixture was stirred for 2 h. The resulting solid was filtered, rinsed with Et$_2$O and dried to afford the title compound, 31, as a yellow solid (68 mg, 61%). $^1$HNMR (400 MHz, DMSO-d$_6$): δ 0.85 (t, 3H), 2.39 (q, 2H), 2.52 (br, 4H), 3.43 (br, 2H), 3.55 (br, 4H), 6.50 (d, J=15.9 Hz, 1H), 6.80 (d, J=8.4 Hz, 2H), 6.85 (d, J=8.6 Hz, 2H), 7.09-7.19 (m, 5H), 7.24 (d, J=8.1 Hz, 2H), 7.58 (d, J=15.9 Hz, 1H), 769 (d, J=8.1 Hz, 2H), 12.33 (br s, 1H); MS m/z 498 (M+H)$^+$.

Prepared in a similar manner as above-described for Example 19 (Scheme 6):

Example 20 (33, Scheme 6)

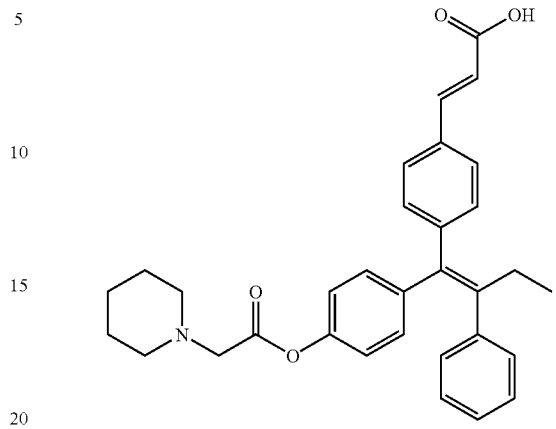

(2E)-3-[4-((1Z)-2-phenyl-1-{4-[(piperidin-1-ylacetyl)oxy]phenyl}but-1-enyl)phenyl]prop-2-enoic acid (33)

Treatment of compound 32 with piperidine as described in Example 19 (Step 2) afforded the title compound, 33, as a light yellow solid (85 mg, 77%). $^1$HNMR (400 MHz, DMSO-d$_6$): δ 0.85 (t, 3H), 1.35 (br, 2H), 1.74 (br, 4H), 2.40 (q, 2H), 3.00 (br, 2H), 3.44 (br, 2H), 4.36 (br, 2H), 6.51 (d, J=16.1 Hz, 1H), 6.87-6.90 (m, 4H), 7.09-7.19 (m, 5H), 7.25 (d, J=8.1 Hz, 2H), 7.58 (d, J=16.1 Hz, 1H), 7.70 (d, J=8.2 Hz, 2H), 10.17 (br, 1H), 12.39 (br, 1H); MS m/z 496 (M+H)$^+$; Anal. calculated for C$_{32}$H$_{33}$N$_1$O$_4$.HCl.1.5H$_2$O: C, 68.74; H, 6.67; N, 2.50; Found: C, 68.31; H, 6.34; N, 2.37.

Example 21 (34, Scheme 6)

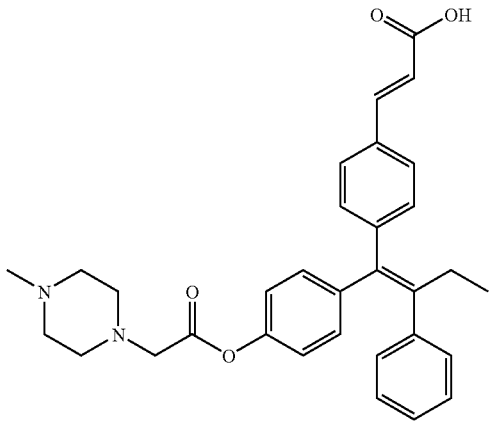

(2E)-3-{4-[(1Z)-1-(4-{[(4-methylpiperazin-1-yl)acetyl]oxy}phenyl)-2-phenylbut-1-enyl]phenyl}prop-2-enoic acid (34)

Treatment of compound 32 with N-methylpiperazine as described in Example 19 (Step 2) afforded the title compound, 34, as an off-white solid. $^1$HNMR (400 MHz, DMSO-d$_6$): δ 0.85 (t, 3H), 2.11 (s, 3H), 2.27 (br, 4H), 2.39 (q, 2H), 2.50 (br, 4H), 3.38 (s, 2H), 6.49 (d, J=16 Hz, 1H), 6.79 (d, J=8.6 Hz, 2H), 6.85 (d, J=8.6 Hz, 2H), 7.09-7.19 (m, 5H), 7.23 (d, J=8.1 Hz, 2H), 7.49 (d, J=16 Hz, 1H), 7.65 (d, J=8 Hz, 2H), 12.36 (br, 1H); MS m/z 511 (M+H)$^+$.

MS, m/z 473 (M+Na)$^+$; Anal. calculated for C$_{25}$H$_{23}$O$_6$P.0.36H$_2$O: C, 65.72; H, 5.23; Found: C, 65.71; H, 5.33.

Example 22 (35, Scheme 7)

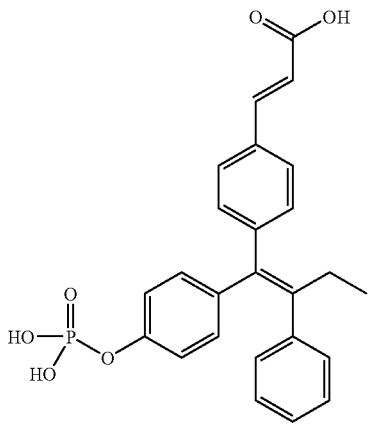

Step 1: tert-Butyl (2E)-3-(4-{(1Z)-2-phenyl-1-[4-(phosphonooxy)phenyl]-1-butenyl}phenyl)-2-propenoate (36)

To a solution of compound 12 (0.34 g, 0.80 mmol) in anhydrous THF (20 mL) at 0° C. was added Et$_3$N (0.24 mL, 0.176 g, 1.74 mmol) and a solution of POCl$_3$ (0.082 mL, 0.134 g, 0.87 mmol) in THF (1 mL). The mixture stirred at 0° C. for 1 h concentrated to ~3 mL and then partitioned between EtOAc and H$_2$O. The organic phase was dried (Na$_2$SO$_4$), concentrated, and the residue was suspended in H$_2$O and stirred at ambient temperature for 3 h. The slurry was extracted with EtOAc and the organic phase was dried (Na$_2$SO$_4$) and concentrated to give 36 (0.40, 99%) as a solid foam. $^1$HNMR (DMSO-d$_6$): δ 0.85 (t, J=7.3 Hz, 3H), 2.30 (q, J=7.3 Hz, 2H), 6.5 (d, J=15.8 Hz, 1H), 6.79 (d, J=9 Hz, 2H), 6.83 (d, J=9 Hz, 2H), 7.08-7.26 (m, 7H), 7.55 (d, J=15.8 Hz, 1H), 7.69 (d, J=8.1 Hz, 2H).

Step 2: (2E)-3-(4-{(1Z)-2-Phenyl-1-[4-(phosphonooxy)phenyl]-1-butenyl}phenyl)-2-propenoic acid (35)

To a solution of 36 (0.40 g) in CH$_2$Cl$_2$ (5 mL) at 0° C. was added dropwise TFA (5 mL) and the mixture was stirred at 0° C. for 2 h. Solvent was evaporated and coevaporated with CH$_2$Cl$_2$ (2×5 mL). The residue was suspended in Et$_2$O/EtOAc (1:4 v/v, 10 mL) and treated with 1 M aqueous NaOH (10 mL). The aqueous phase was separated and acidified (pH ~ 2-3) with aqueous HCl. The mixture was extracted with EtOAc and the organic layer was dried (Na$_2$SO$_4$) and concentrated. The resulting solid foam was dissolved in a small amount EtOAc and then excess hexanes added. After stirring for 20 min, the precipitate was filtered and washed with hexanes to provide 35 (0.31 g, 86%) as a pale yellow solid, mp 181-183° C. $^1$HNMR (CD$_3$OD): δ 0.92 (t, J=7.1 Hz, 3H), 2.47 (q, J=7.1 Hz, 2H), 6.49 (d, J=16 Hz, 1H), 6.82-6.87 (m, 4H), 7.03-7.21 (m, 5H), 7.27 (d, J=7.8 Hz, 2H), 7.6 (d, J=7.8 Hz, 2H), 7.69 (d, J=16 Hz, 1H); $^{31}$PNMR (CD$_3$OD): δ −4.06 (s);

Example 23 (37, Scheme 8, Method A)

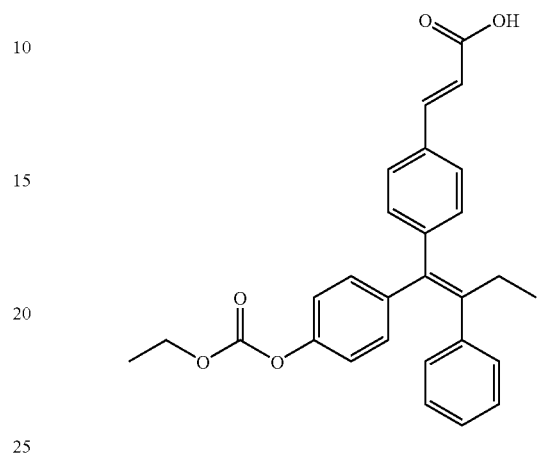

Step 1: tert-Butyl (2E)-3-{4-[(1Z)-1-(4-{[(4-nitrophenoxy)carbonyl]oxy}phenyl)-2-phenyl-1-butenyl]phenyl}-2-propenoate (38)

To a solution of compound 12 (0.5 g, 1.17 mmol, ~9:1 Z/E ratio by $^1$HNMR) in CH$_2$Cl$_2$ (10 mL) was added p-nitrophenyl chloroformate (0.35 g, 1.76 mmol) and pyridine (0.29 mL, 0.28 g, 3.58 mmol). The reaction mixture was stirred at ambient temperature for 18 h and then concentrated. The residue was purified by chromatography (silica gel, hexanes/EtOAc, 8:1) to provide 38 (0.63 g, 91%, ~9:1 Z/E mixture) as a cream-colored solid foam. $^1$HNMR (400 MHz, DMSO-d$_6$): δ 0.85 (t, J=7.4 Hz, 3H), 1.42 (s, 9H), 2.39 (q, J=7.4 Hz, 2H), 6.50 (d, J=16 Hz, 1H), 6.92 (d, J=8.6 Hz, 2H), 7.1-7.8 (m, 14H), 8.3-8.4 (m, 2H).

Step 2: (2E)-3-[4-((1Z)-1-{4-[(Ethoxycarbonyl)oxy]phenyl}-2-phenyl-1-butenyl)phenyl]-2-propenoic acid (37)

To a solution of 38 (0.050 g, 0.084 mmol) in CH$_2$Cl$_2$ (2 mL) was added EtOH (0.050 g, 1.08 mmol) and Et$_3$N (0.016 g, 0.16 mmol). The mixture was stirred at ambient temperature for 18 h, diluted with CH$_2$Cl$_2$, washed with water and 0.1 N hydrochloric acid, dried (Na$_2$SO$_4$), and concentrated. The residue was separated by preparative RP-HPLC (C-18 Luna column, 85% MeCN/H$_2$O/0.1% TFA) and the corresponding fractions were concentrated. The residue was dissolved in CH$_2$Cl$_2$ (0.3 mL) and cooled to 0° C. TFA (0.3 mL) was added and the mixture stirred at 0° C. for 1 h. The solvent was evaporated and co-evaporated with CH$_2$Cl$_2$ (2×10 mL) and the residue crystallized from a small amount of EtOAC to provide 37 (0.010 g) as an off-white solid; mp 135-136° C.; $^1$HNMR (DMSO-d$_6$): δ 0.85 (t, J=7.2 Hz, 3H), 1.21 (t, J=7.2 Hz, 3H), 2.39 (q, J=7.2 Hz, 2H), 4.15 (q, J=7.2 Hz, 2H), 6.5 (d, J=16 Hz, 1H), 6.85 (d, J=9 Hz, 2H), 6.89 (d, J=9 Hz, 2H), 7.08-7.22 (m, 5H), 7.24 (d, J=7.9 Hz, 2H), 7.58 (d, J=16 Hz, 1H), 7.69 (d, J=7.9 Hz, 2H), 12.45 (br s, 1H); MS, m/z 465 (M+Na)$^+$; Anal. calculated for C$_{28}$H$_{26}$O$_5$.0.13H$_2$O: C, 75.60; H, 5.95; Found: C, 75.61; H, 5.93.

Example 24 (37, Scheme 9, Method B)

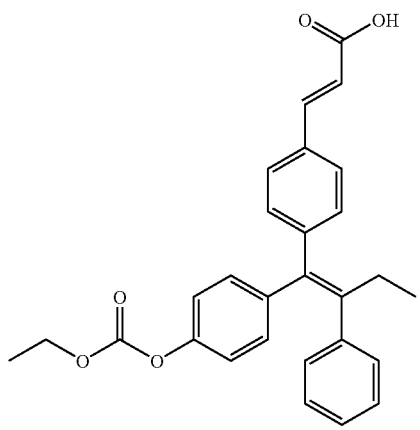

Step 1: tert-butyl (2E)-3-[4-((1Z)-1-{4-[(ethoxycarbonyl)oxy]phenyl}-2-phenyl-1-butenyl)phenyl]-2-propenoate (39)

To a solution of tert-butyl ester 12 (0.45 g, 1.06 mmol) in $CH_2Cl_2$ (20 mL) at 0° C. was added $Et_3N$ (0.32 mL, 0.23 g, 2.33 mmol) and ethyl chloroformate (0.115 mL, 0.126 g, 1.16 mmol) and the mixture stirred at ambient temperature for 1 h. The mixture was washed with ice-chilled 0.1 N hydrochloric acid and the organic layer dried ($Na_2SO_4$) and evaporated to provide compound 39 as an off-white solid (0.52 g, 99%); $^1$H NMR (DMSO-$d_6$): δ 0.86 (t, J=7.1 Hz, 3H), 1.23 (t, J=7.5 Hz, 3H), 1.48 (s, 9H), 2.40 (q, J=7.5 Hz, 2H), 4.17 (q, J=7.1 Hz, 2H), 6.51 (d, J=16 Hz, 1H), 6.87 (d, J=9 Hz, 2H), 6.91 (d, J=9 Hz, 2H), 7.10-7.16 (m, 3H), 7.18-7.22 (m, 2H), 7.25 (d, J=8.1 Hz, 2H), 7.55 (d, J=16 Hz, 1H), 7.71 (d, J=8.1 Hz, 2H); MS, m/z 521 (M+Na)$^+$.

Step 2: (2E)-3-[4-((1Z)-1-{4-[(Ethoxycarbonyl)oxy]phenyl}-2-phenyl-1-butenyl)phenyl]-2-propenoic acid (37)

To a solution of 39 (0.51 g, 1.02 mmol) in $CH_2Cl_2$ (5 mL) at 0° C. was added TFA (5 mL) and the mixture was stirred for 1 h. Solvent was evaporated and coevaporated with $CH_2Cl_2$ (2×10 mL) and the residue dissolved in EtOAc and washed with water (2×10 mL). The organic layer was dried ($Na_2SO_4$) and evaporated. The residue was triturated with hexanes, filtered, and dried in vacuo to provide 37 (0.43 g, 96%) as an off-white solid. $^1$H NMR and MS as described in Example 23. Anal. calculated for $C_{28}H_{26}O_5$: C, 76.00; H, 5.92; Found: C, 75.90; H, 6.12.

Example 25 (40, Scheme 9, Method B)

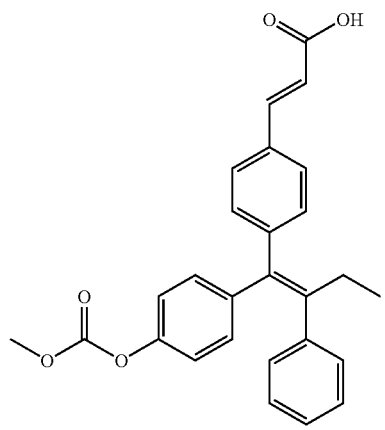

(2E)-3-[4-((1Z)-1-{4-[(Methoxycarbonyl)oxy]phenyl}-2-phenyl-1-butenyl)phenyl]-2-propenoic acid (40)

The title compound was prepared from 12 and methylchloroformate similar to the procedure described for Example 24. Off-white solid; mp 140-142° C.; $^1$HNMR (DMSO-$d_6$): δ 0.86 (t, J=7.4 Hz, 3H), 2.40 (q, J=7.4 Hz, 2H), 3.75 (s, 3H), 6.51 (d, J=16 Hz, 1H), 6.87 (d, J=8.7 Hz, 2H), 6.90 (d, J=8.7 Hz, 2H), 7.10-7.22 (m, 5H), 7.26 (d, J=8.1 Hz, 2H), 7.59 (d, J=16 Hz, 1H), 7.7 (d, J=8.1 Hz, 2H), 12.45 (br s, 1H); MS, m/z 451 (M+Na)$^+$; Anal. calculated for $C_{27}H_{24}O_5 \cdot 0.65H_2O$: C, 73.67; H, 5.79; Found: C, 73.66; H, 5.85.

Biological Data

Competition Binding Assay:

Recombinant full length human ERα and ERβ protein was purchased from PanVera (PanVera-Invitrogen Discovery Screening, Discovery Center, 501 Charmany Drive, Madison, Wis. 53719, USA). Polylysine coated Yttrium Silicate SPA beads (Amersham #RPNQ 0010) are resuspended in assay buffer [10 mM potassium phosphate buffer pH 7.0 containing 2 mM EDTA, 50 mM NaCl, 1 mM DTT, 2 mM CHAPS, 10% glycerol] to a concentration of 1 g/60 ml. 30 μl (0.5 mg) of the SPA beads are then added to each well of a Packard OptiPlate (Packard 6005190, Packard Instruments, Meriden, Conn.). The ERα or ERβ protein is diluted to the appropriate concentration (empirically determined for each protein prep by generating a protein curve using 0.5 to 10 μg total protein and 1 nM [3H] Estradiol and selecting a protein concentration that does not deplete the radioligand) and added as 30 μl aliquots to each well. [2, 4, 6, 7, 16, 17-3H(N)]-Estradiol is added as a 30 μl aliquot to give a final assay concentration of 1 nM. To give a final volume of 100 μl, either 10 μl of a test compound solution (typically in 10% DMSO as solvent), solvent containing no test compound (to determine total binding, T), or solvent containing 17-b-estradiol at 100 μM (to determine non-specific binding, NS) are finally added to the plate. The plates are shaken vigorously for two hours then counted on a Packard TopCount using the protocol for counting tritium yttrium silicate SPA beads. Data analysis was done by standard methods.

% Bound was calculated for each concentration of each test compound using the equation % Bound=100*((Test−NS)/(T−NS)).

% Bound was plotted vs concentration and curve fitting was accomplished using non-linear regression.

At least two binding curves were generated.

The pKi values for compound 1 were determined to be about 7.56 vs. estrogen receptor (ER) ER-alpha and ER-beta.

Test compounds were employed in free or salt form.

All research complied with the principles of laboratory animal care (NIH publication No. 85-23, revised 1985) and GlaxoSmithKline policy on animal use.

Pharmacokinetic Data

In order to study the pharmacokinetic behavior of the prodrugs of this invention, a single oral dose of a series of prodrugs as well as compound 1 was administered to female CD (Charles River Sprague Dawley) rats. Rats received each compound by oral gavage at a dose of 10 mg/kg. The compound was administered as a suspension in a vehicle composed of an aqueous solution containing 0.5% hydroxypropylmethylcellulose (HPMC) and 0.1% polysorbate 80 (Tween 80). The bioavailability of compound 1 (also referred to as the "parent drug") and prodrugs of 1 are listed in Table I.

TABLE I

Rat Bioavailability of Compound 1 and Prodrugs

| Compound | R | Bioavailability of 1 in Rat (% F)[1] |
|---|---|---|
| 1 | H | 5.7 (29.0[2]) |
| 7 | H₃C-C(=O)- (acetyl) | 86.6 |
| 26 | MeO-CH₂CH₂-C(=O)- | 52.4 |
| 25 | 2-thienyl-C(=O)- | 50.9 |
| 37 | EtO-C(=O)- | 43.2 |
| 24 | isoxazol-5-yl-C(=O)- | 43.2 |
| 23 | (CH₃)₂N-CH₂-C(=O)- | 38.3 |
| 35 | PO₃H₂ | 37.0 |
| 27 | F₃C-CH₂CH₂-C(=O)- | 28.9 |
| 40 | MeO-C(=O)- | 21.9 |
| 31 | morpholino-CH₂-C(=O)- | 21.3 |
| 21 | H₃C-CH₂CH₂-C(=O)- | 18.2 |
| 22 | 2-furyl-C(=O)- | 16.9 |
| 33 | piperidino-CH₂-C(=O)- | 13.9 |
| 20 | H₃C-CH₂-C(=O)- | 13.5 |
| 34 | 4-Me-piperazin-1-yl-CH₂-C(=O)- | 13.4 |
| 18 | phenyl-C(=O)- | 12.3 |
| 28 | (CH₃)₃C-C(=O)- | 3.5 |
| 29 | cyclohexyl-CH₂-C(=O)- | 3.3 |

(No prodrug was detected in plasma at t = 15 min (first data point))

[1] Unless noted otherwise, the compound was administered as a suspension in a vehicle composed of an aqueous solution containing 0.5% hydroxypropylmethylcellulose (HPMC) and 0.1% polysorbate 80 (Tween 80).

[2] Compound administered as a solution in a vehicle composed of an aqueous solution containing 20% hydroxypropoylcyclodextrin.

The tablulated data above illustrates that administration of prodrugs of 1 of the present invention in an aqueous suspension provide a significant and unexpected improvement in bioavailability relative to the parent drug (1). As demonstrated, the observed improvement in bioavailablility could not be predicted based on structural similarities of the prodrugs. For example, the closely related alkyl ester prodrugs 28, 20, 21 and 7 display an almost 30-fold range in bioavailability (see, Table I).

Traditionally, prodrugs have often been used to increase the bioavailability of a drug via improvement of prodrug solubility by attaching a water-soluble moiety (the "pro-group") to a poorly water soluble parent drug (D. Fleisher, *Adv. Drug Del. Rev.* (1996) 19, 115-130, incorporated herein by reference). In the present invention, however, Table II demonstrates no correlation between solubility in fasted state simulated intestinal fluid (SIF) and oral bioavailability (see below Table II). The poor solubility of the compounds in Table II was observed in other solubility tests as well, including standard phosphate buffer (pH=7.4) as well as 0.1 N aqueous HCl (data not shown).

TABLE II

Aqueous Solubility and Oral Bioavailability of Compound 1 and Prodrugs

| Compound | R | SIF Solubility[3] | Bioavailability of 1 in Rat[4] |
|---|---|---|---|
| 1 | H | 0.023 | 5.7 |
| 35 | $PO_3H_2$ | >1.0 | 37.0 |
| 20 |  | 0.129 | 13.5 |
| 7 |  | 0.061 | 86.6 |
| 21 |  | 0.021 | 18.2 |
| 23 |  | 0.015 | 38.3 |

[3] Equilibrium solubility is expressed in mg/ml and was determined in fasted state simulated intestinal fluid (SIF, pH = 6.8) using a slightly modified version of the formulation reported by Galia et al, 1998.
[4] Bioavailability expressed as % F. Unless noted otherwise, the compound was administered as a suspension in a vehicle composed of an aqueous solution containing 0.5% hydroxypropylmethylcellulose (HPMC) and 0.1% polysorbate 80 (Tween 80).

As described herein, prodrugs of 1 were identified that demonstrate significant and unexpected increases in oral bioavailability of 1 in vivo in a suspension formulation, despite the solubility in fasted state simulated intestinal fluid. Thus, although unpredictable, prodrugs of the present invention have the potential to deliver a compound that is particularly useful for selective estrogen receptor modulation in a standard solid dosage form that is orally administrable, such as a tablet or a capsule or a suspension.

Although specific embodiments of the present invention are herein illustrated and described in detail, the invention should not necessarily be limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

What is claimed is:

1. A compound of formula (I):

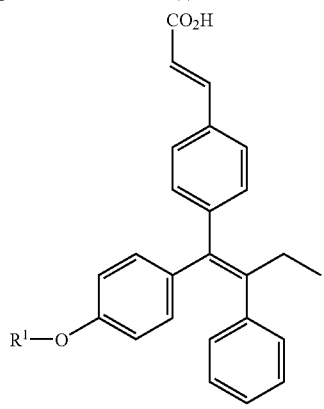

(I)

including pharmacologically functional salts and solvates thereof, wherein $R^1$ is —C(O)-alkyl, —C(O)-aryl, —C(O)-heteroaryl, —C(O)-cycloalkyl, —C(O)—$(CH_2)_n$—$NR^4R^5$, —C(O)—O-alkyl, —C(O)—$(CH_2)_n$—O-alkyl, —C(O)—$(CH_2)_n$-haloalkyl, —C(O)—$(CH_2)_n$-heterocylcyl, or —$PO_3H_2$;

$R^4$ and $R^5$ each independently are selected from H and alkyl; and n is 1 to 6.

2. The compound of claim 1 wherein alkyl is $C_1$-$C_6$ alkyl; aryl is phenyl; heteroaryl is thienyl, isoxazoyl, or furyl; cycloalkyl is $C_1$-$C_6$ cycloalkyl, haloalkyl is $C_1$-$C_6$ haloalkyl, and heterocyclyl is morpholinyl or optionally substituted piperizinyl.

3. The compound of claim 1 wherein $R^1$ is —C(O)—$C_{1-6}$alkyl.

4. The compound of claim 1, wherein the compound is (2E)-3-(4-{(1Z)-2-phenyl-1-[4-(propionyloxy)phenyl]but-1-enyl}phenyl)prop-2-enoic acid, including pharmaceutically acceptable salts and solvates thereof.

5. The compound of claim 1, wherein the compound is (2E)-3-(4-{(1Z)-2-Phenyl-1-[4-(phosphonooxy)phenyl]-1-butenyl}phenyl)-2-propenoic acid, including pharmaceutically acceptable salts solvates thereof.

6. The compound of claim 3 wherein $R^1$ is —C(O)—$CH_2$—$CH_3$.

7. A compound selected from
(2E)-3-(4-{(1Z)-2-phenyl-1-[4-(propionyloxy)phenyl]but-1-enyl}phenyl)prop-2-enoic acid;
(2E)-3-(4-{(1Z)-1-[4-(benzoyloxy)phenyl]-2-phenylbut-1-enyl}phenyl)prop-2-enoic acid;
(2E)-3-(4-{(1Z)-1-[4-(acetyloxy)phenyl]-2-phenyl but-1-enyl}phenyl)prop-2-enoic acid;
(2E)-3-(4-{(1Z)-1-[4-(butyryloxy)phenyl]-2-phenylbut-1-enyl}phenyl)prop-2-enoic acid;
(2E)-3-(4-{(1Z)-1-[4-(2-Furoyloxy)phenyl]-2-phenyl-1-butenyl}phenyl)-2-propenoic acid;
(2E)-3-[4-((1Z)-1-{4-[(N,N-dimethylglycyl)oxy]phenyl}-2-phenylbut-1-enyl)phenyl]prop-2-enoic acid;
(2E)-3-[4-((1Z)-1-{4-[(5-Isoxazolylcarbonyl)oxy]phenyl}-2-phenyl-1-butenyl)phenyl]-2-propenoic acid;
(2E)-3-[4-((1Z)-2-phenyl-1-{4-[(thien-2-ylcarbonyl)oxy]phenyl}but-1-enyl)phenyl]prop-2-enoic acid;
(2E)-3-[4-((1Z)-1-{4-[(methoxyacetyl)oxy]phenyl}-2-phenylbut-1-enyl)phenyl]prop-2-enoic acid;
(2E)-3-[4-((1Z)-2-phenyl-1-{4-[(4,4,4-trifluorobutanoyl)oxy]phenyl}but-1-enyl)phenyl]prop-2-enoic acid;
(2E)-3-[4-((1Z)-1-{4-[(2,2-dimethylpropanoyl)oxy]phenyl}-2-phenyl but-1-enyl)phenyl]prop-2-enoic acid;
(2E)-3-[4-((1Z)-1-{4-[(cyclohexylcarbonyl)oxy]phenyl}-2-phenylbut-1-enyl)phenyl]prop-2-enoic acid;
(2E)-3-[4-((1Z)-1-{4-[(morpholin-4-ylacetyl)oxy]phenyl}-2-phenylbut-1-enyl)phenyl]prop-2-enoic acid;
(2E)-3-[4-((1Z)-2-phenyl-1-{4-[(piperidin-1-ylacetyl)oxy]phenyl}but-1-enyl)phenyl]prop-2-enoic acid;
(2E)-3-{4-[(1Z)-1-(4-{[(4-methylpiperazin-1-yl)acetyl]oxy}phenyl)-2-phenylbut-1-enyl]phenyl}prop-2-enoic acid;
(2E)-3-(4-{(1Z)-2-Phenyl-1-[4-(phosphonooxy)phenyl]-1-butenyl}phenyl)-2-propenoic acid;
(2E)-3-[4-((1Z)-1-{4-[(Ethoxycarbonyl)oxy]phenyl}-2-phenyl-1-butenyl)phenyl]-2-propenoic acid; and
(2E)-3-[4-((1Z)-1-{4-[(Methoxycarbonyl)oxy]phenyl}-2-phenyl-1-butenyl)phenyl]-2-propenoic acid, including pharmaceutically acceptable salts and solvates thereof.

8. A pharmaceutical composition comprising a compound according to claim 1, and a pharmaceutically acceptable carrier.

9. A method for the treatment of conditions or disorders selected from menopausal or postmenopausal disorders, vasomotor symptoms, urogenital or vulvar vaginal atrophy, atrophic vaginitis, female sexual dysfunction, breast cancer, depressive symptoms, diabetes, bone demineralization, and osteoporosis comprising the administration of a compound according to claim 1.

10. A process for making ester prodrugs of compound 1:

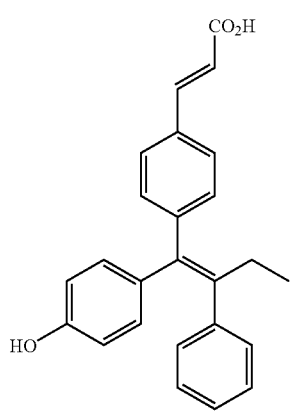

compound 1 comprising:
acylating anisole with 2-phenylbutanoic acid followed by demethylation to yield phenol 8:

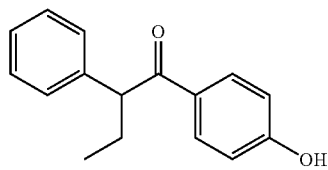

phenol 8 protecting the phenol group;

treating the protected compound with an organometallic reagent followed by dehydration to yield phenol aldehyde 10:

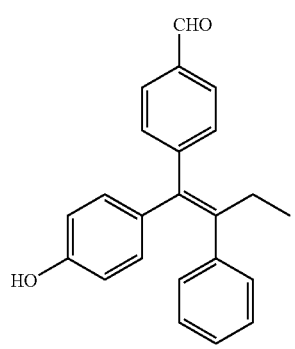

phenol aldehyde 10 acylating phenol aldehyde 10 with an anhydride or an acid chloride in the presence of a base to yield ester intermediate IV:

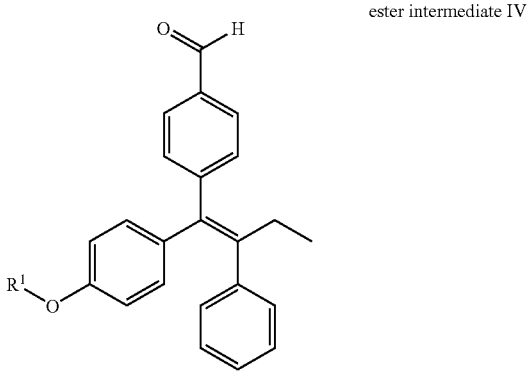

ester intermediate IV wherein $R^1$ is —C(O)-alkyl, —C(O)-aryl, —C(O)-heteroaryl, or —C(O)-cycloalkyl; and treating the ester intermediate IV with malonic acid to yield ester prodrug V:

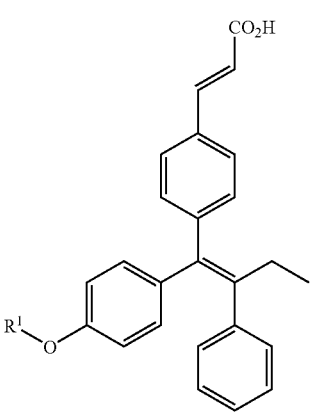

ester prodrug V wherein $R^1$ is as described.

11. The process of claim 10 wherein $R^1$ is —C(O)-alkyl.

12. The process of claim 11 wherein $R^1$ is —C(O)—$C_{1-6}$alkyl.

13. The process of claim 12 wherein $R^1$ is —C(O)—$CH_2CH_3$.

14. The process of claim 10 wherein the step of acylating anisole with 2-phenylbutanoic acid further comprises acid catalyzed acylation of anisole with the mixed anhydride of trifluoroacetic acid and 2-phenylbutanoic acid, followed by treatment with aluminum chloride in an appropriate solvent.

15. The process of claim 10 wherein the step of protecting the phenol group of phenol 8 further comprises protecting phenol 8 as a THP ether 9:

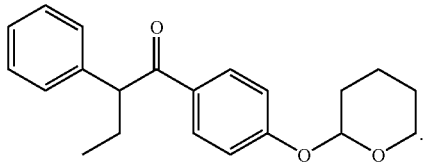

ether 9

16. The process of claim 15 wherein the step of treating the protected compound with an organometallic reagent further comprises treating ether 9 with [4-(dimethoxymethyl)phenyl] lithium or [4-(diethoxymethyl)phenyl] lithium followed by acid catalyzed dehydration.

17. The process of claim 10 wherein the step of acylating phenol aldehyde 10 with an anhydride or an acid chloride in the presence of a base to yield ester intermediate IV is instead comprised of treating the phenol aldehyde 10 with malonic acid to yield ester intermediate IV.

18. An intermediate of formula IV:

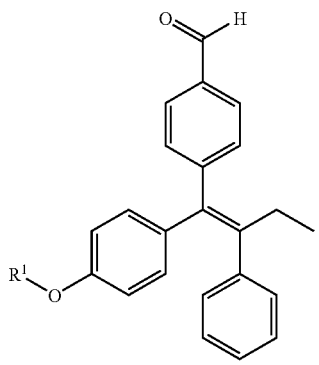

wherein $R^1$ is —C(O)-alkyl, —C(O)-aryl, —C(O)-heteroaryl, or —C(O)-cycloalkyl.

19. The intermediate of claim 18 wherein $R^1$ is —C(O)-alkyl.

20. The intermediate of claim 19 wherein $R^1$ is —C(O)—$C_{1-6}$alkyl.

21. The intermediate of claim 20 wherein $R^1$ is —C(O)—$CH_2CH_3$.

* * * * *